United States Patent
Ramamurthy et al.

(10) Patent No.: US 10,858,593 B2
(45) Date of Patent: Dec. 8, 2020

(54) CONVERSION OF WASTE PLASTIC TO PROPYLENE AND CUMENE

(71) Applicant: SABIC Global Technologies B.V., Bergen op Zoom (NL)

(72) Inventors: Krishna Kumar Ramamurthy, Bengaluru (IN); Ravichander Narayanaswamy, Bengaluru (IN); Venkata Ramanarayanan Ganapathy Bhotla, Bangalore (IN); Alexander Stanislaus, Bangalore (IN); Santosh Ganji, Bangalore (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 25 days.

(21) Appl. No.: 16/467,727

(22) PCT Filed: Jan. 3, 2018

(86) PCT No.: PCT/IB2018/050048
§ 371 (c)(1),
(2) Date: Jun. 7, 2019

(87) PCT Pub. No.: WO2018/127817
PCT Pub. Date: Jul. 12, 2018

(65) Prior Publication Data
US 2019/0367428 A1 Dec. 5, 2019

Related U.S. Application Data

(60) Provisional application No. 62/442,679, filed on Jan. 5, 2017.

(51) Int. Cl.
*C07C 2/66* (2006.01)
*C07C 6/04* (2006.01)
(Continued)

(52) U.S. Cl.
CPC ............ *C10G 1/002* (2013.01); *C07C 2/66* (2013.01); *C07C 4/06* (2013.01); *C08J 11/12* (2013.01);
(Continued)

(58) Field of Classification Search
None
See application file for complete search history.

(56) References Cited

U.S. PATENT DOCUMENTS

| 5,026,936 A | 6/1991 | Leyshon et al. |
| 6,916,448 B2 | 7/2005 | Commereuc et al. |

(Continued)

FOREIGN PATENT DOCUMENTS

| CN | 101848880 B | 7/2013 |
| CN | 103269791 B | 9/2015 |

(Continued)

OTHER PUBLICATIONS

International Search Report and Written Opinion from PCT/IB2018/050048 dated Apr. 10, 2018, 10 pages.

*Primary Examiner* — Philip Y Louie
(74) *Attorney, Agent, or Firm* — Norton Rose Fulbright US LLP

(57) ABSTRACT

A process for producing cumene comprising converting plastics to hydrocarbon liquid and pyrolysis gas; feeding hydrocarbon liquid to hydroprocessor to yield hydrocarbon product and first gas stream; feeding hydrocarbon product to reforming unit to produce reforming product, second gas stream, and hydrogen; separating reforming product into non-aromatics recycle stream and second aromatics stream ($C_6+$ aromatics); recycling non-aromatics recycle stream to reforming unit; separating second aromatics stream into benzene, $C_7$, $C_8$, $C_9$, $C_{10}$, and $C_{11}+$ aromatics; contacting $C_7$, $C_9$, and/or $C_{10}$ aromatics with a
(Continued)

disproportionation&transalkylation catalyst/H2 to yield benzene&xylenes; conveying $C_{11}+$ aromatics to hydroprocessor; introducing pyrolysis gas, first and/or second gas stream to first separator to produce first propylene stream, first $C_2$&$C_4$ unsaturated stream, and saturated gas ($H_2$ and $C_{1-4}$ saturated hydrocarbons); introducing first $C_2$&$C_4$ unsaturated stream to metathesis reactor to produce second propylene stream; and feeding benzene, and first and/or second propylene stream to alkylation unit to produce cumene.

20 Claims, 6 Drawing Sheets

(51) Int. Cl.

| | |
|---|---|
| *C07C 6/10* | (2006.01) |
| *C10G 1/00* | (2006.01) |
| *C07C 4/06* | (2006.01) |
| *C08J 11/12* | (2006.01) |
| *C10G 1/10* | (2006.01) |
| C07C 11/06 | (2006.01) |
| C07C 15/04 | (2006.01) |
| C07C 15/085 | (2006.01) |

(52) U.S. Cl.
CPC ............... *C10G 1/10* (2013.01); *C07C 11/06* (2013.01); *C07C 15/04* (2013.01); *C07C 15/085* (2013.01)

(56) References Cited

U.S. PATENT DOCUMENTS

| | | |
|---|---|---|
| 8,895,790 B2 | 8/2014 | Narayanaswamy et al. |
| 2006/0089517 A1 | 4/2006 | Podrebarac et al. |
| 2009/0227823 A1 | 9/2009 | Huber et al. |
| 2014/0228606 A1* | 8/2014 | Narayanaswamy ... C10G 69/08 585/241 |
| 2015/0141700 A1* | 5/2015 | Johnson ................. C07C 2/864 568/385 |
| 2016/0304788 A1* | 10/2016 | Sorensen ............. C08G 63/183 |

FOREIGN PATENT DOCUMENTS

| | | |
|---|---|---|
| JP | H11138125 A | 5/1999 |
| JP | 2005154510 A | 6/2005 |
| JP | 2007302788 A | 11/2007 |
| JP | 4943816 B2 | 5/2012 |
| KR | 20140107559 A | 9/2014 |
| WO | WO2007043738 A1 | 4/2007 |
| WO | WO2016142808 A1 | 9/2016 |

\* cited by examiner

CONVERSION OF WASTE PLASTIC TO PROPYLENE AND CUMENE

This application is a national phase application under 35 U.S.C. § 371 of International Application No. PCT/IB2018/050048 filed Jan. 3, 2018, which claims priority to U.S. Provisional Patent Application No. 62/442,679 filed Jan. 5, 2017. The entire contents of each of the above-referenced disclosures is specifically incorporated by reference herein without disclaimer.

TECHNICAL FIELD

This disclosure relates to the production of high value products, such as aromatic hydrocarbons from mixed plastics via processes which include pyrolysis, hydroprocessing, reforming, disproportionation, alkylation, and olefin metathesis, wherein cumene is the preferred product.

BACKGROUND

Cumene is an important chemical intermediate, with almost all produced cumene being converted to cumene hydroperoxide, which is an intermediate in the synthesis of other industrially important chemicals, such as phenol and acetone, which can be further used in the production of bisphenol A. Current processes for producing cumene convert petroleum feedstock to benzene and propylene, which are then reacted to form cumene. The cumene produced from intermediates derived from petroleum feedstock is expensive, and as a result impacts the economics of the bisphenol A production process. Thus, there is an ongoing need to develop methods for producing cumene from feedstocks other than crude oil, for example from feedstocks derived from waste plastics.

BRIEF SUMMARY

Disclosed herein is a process for producing cumene comprising (a) converting a plastic waste to a hydrocarbon liquid stream and a pyrolysis gas stream in a pyrolysis unit, (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons, (c) feeding at least a portion of the hydrocarbon product to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the hydrocarbon product, (d) introducing at least a portion of the reforming unit product to a second aromatics separating unit to produce a non-aromatics recycle stream and a second aromatics stream, wherein the second aromatics stream comprises $C_6+$ aromatic hydrocarbons, (e) recycling at least a portion of the non-aromatics recycle stream to the reforming unit, (f) introducing at least a portion of the second aromatics stream to a third aromatics separating unit to produce a benzene stream, a $C_7$ aromatics stream, a $C_8$ aromatics stream, a $C_9$ aromatics stream, a $C_{10}$ aromatics stream, and a $C_{11}+$ aromatics stream, wherein the benzene stream comprises benzene, wherein the $C_7$ aromatics stream comprises toluene, and wherein the $C_8$ aromatics stream comprises xylenes and ethylbenzene, (g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes, (h) conveying at least a portion of the $C_{11}+$ aromatics stream to the hydroprocessing unit, (i) introducing at least a portion of the pyrolysis gas stream, at least a portion of the first gas stream, at least a portion of the second gas stream, or combinations thereof to a first separating unit to produce a first propylene stream, a first $C_2$ and $C_4$ unsaturated stream, and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons, (j) feeding at least a portion of the first $C_2$ and $C_4$ unsaturated stream to a metathesis reactor to produce a second propylene stream, wherein the metathesis reactor comprises a metathesis catalyst, and wherein the second propylene stream comprises propylene, and (k) feeding at least a portion of the benzene stream, and at least a portion of the first propylene stream and/or at least a portion of the second propylene stream to an alkylation unit to produce cumene, wherein the alkylation unit comprises an alkylation catalyst.

Also disclosed herein is a process for producing cumene comprising (a) converting a first plastic waste to a first hydrocarbon liquid stream and a first pyrolysis gas stream in a first pyrolysis unit, (b) optionally contacting at least a portion of the first hydrocarbon liquid stream with a first hydroprocessing catalyst in the presence of hydrogen in a first hydroprocessing unit to yield a first hydrocarbon product and a first $C_{1-4}$ gas stream, wherein the first hydrocarbon product comprises $C_5+$ hydrocarbons, (c) recycling at least a portion of the first hydrocarbon liquid stream and/or at least a portion of the first hydrocarbon product to the first pyrolysis unit, (d) converting a second plastic waste to a second hydrocarbon liquid stream and a second pyrolysis gas stream in a second pyrolysis unit, (e) contacting at least a portion of the second hydrocarbon liquid stream with a second hydroprocessing catalyst in the presence of hydrogen in a second hydroprocessing unit to yield a second hydrocarbon product and a second $C_{1-4}$ gas stream, wherein the second hydrocarbon product comprises $C_5$ to $C_8$ hydrocarbons, and wherein the first hydroprocessing catalyst and the second hydroprocessing catalyst are the same or different, (f) feeding at least a portion of the second hydrocarbon product to a reforming unit to produce a reforming unit product, a third $C_{1-4}$ gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the second hydrocarbon product, (g) introducing at least a portion of the reforming unit product to a second aromatics separating unit to produce a non-aromatics recycle stream and a second aromatics stream, wherein the second aromatics stream comprises $C_6+$ aromatic hydrocarbons, (h) recycling at least a portion of the non-aromatics recycle stream to the reforming unit, (i) introducing at least a portion of the second aromatics stream to a third aromatics separating unit to produce a benzene stream, a $C_7$ aromatics stream, a $C_8$ aromatics stream, a $C_9$ aromatics stream, a $C_{10}$ aromatics stream, and a $C_{11}+$ aromatics stream, wherein the benzene stream comprises benzene, wherein the $C_7$ aromatics stream comprises toluene, and wherein the $C_8$ aromatics stream comprises xylenes and ethylbenzene, (j) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes, (k) conveying at least a portion of the $C_{11}+$ aromatics stream to the first hydroprocessing unit and/or the second hydroprocessing unit, (l) introducing at least a portion of the first pyrolysis gas stream, at least a portion of the second pyrolysis gas stream, at least a portion of the first $C_{1-4}$ gas stream, at least a portion of the second $C_{1-4}$ gas stream, at least a portion of the third $C_{1-4}$ gas stream, or combinations thereof to a first separating unit to produce a first propylene stream, a first $C_2$ and $C_4$ unsaturated stream, and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons, (m) feeding at least a portion of the first $C_2$ and $C_4$ unsaturated stream to a metathesis reactor to produce a second propylene stream, wherein the metathesis reactor comprises a metathesis catalyst, and wherein the second propylene stream comprises propylene, and (n) feeding at least a portion of the benzene stream, and at least a portion of the first propylene stream and/or at least a portion of the second propylene stream to an alkylation unit to produce cumene, wherein the alkylation unit comprises an alkylation catalyst.

DETAILED DESCRIPTION

Figure 1A:
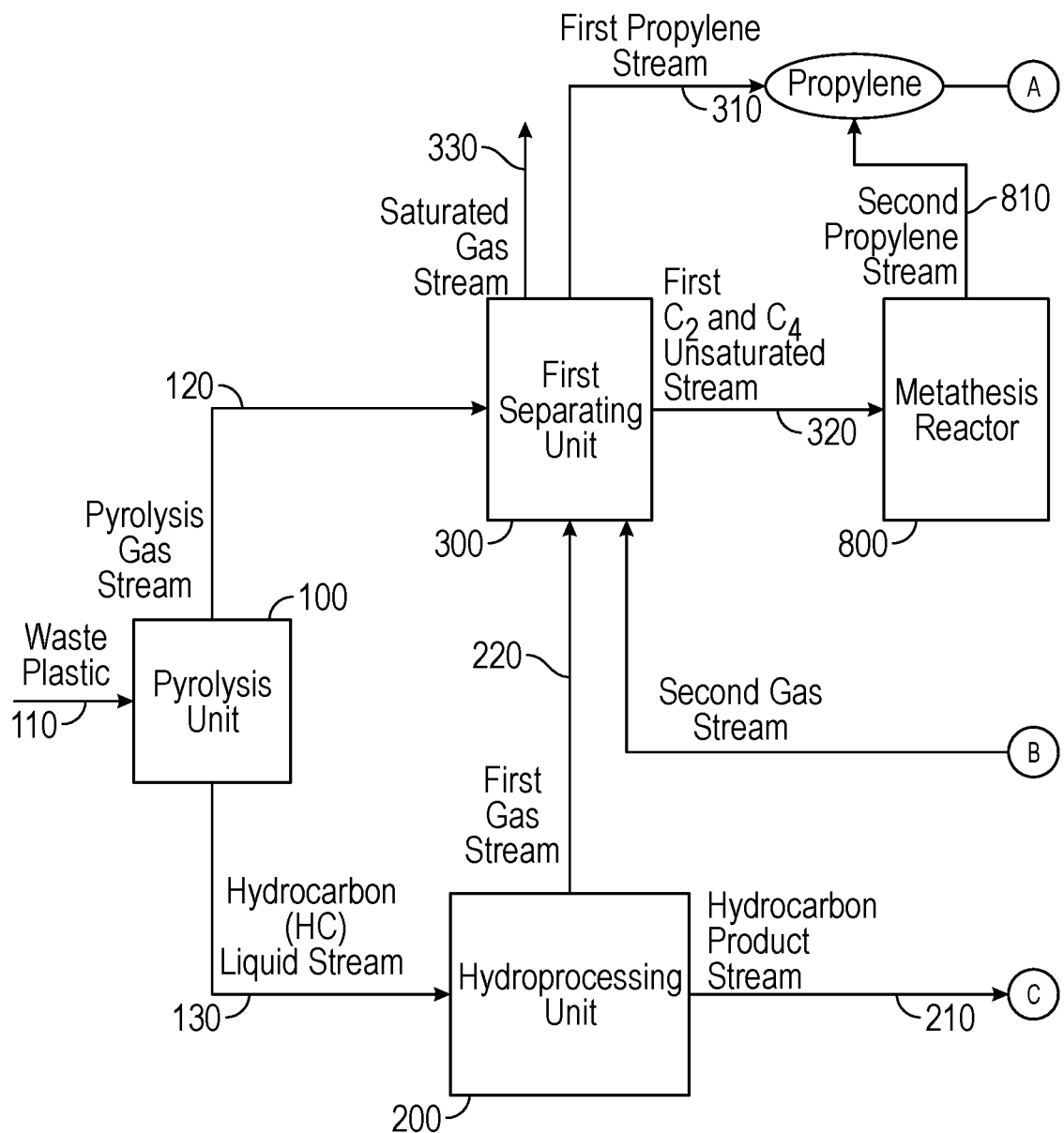
FIGS. 1A and 1B display a configuration of a system for producing cumene.

Disclosed herein are processes and systems for producing high value products such as cumene by processing plastic waste. The process may include conversion of waste plastic, which can be cracked or pyrolyzed by means of low temperature or high temperature pyrolysis, and by thermal or catalytic pyrolysis, wherein the composition of a pyrolysis product can be varied to maximize desired products by varying process conditions and catalysts. The pyrolysis can be configured to maximize propylene and/or aromatics, with high yields of benzene, toluene, xylenes (BTX), and ethylbenzene (EB). To maximize benzene production, the liquid obtained from low severity and/or high severity pyrolysis can be further hydrocracked and/or hydrotreated to reduce a boiling point of the heavies (e.g., heavies can be cracked to mostly $C_{10-}$ hydrocarbons), and to also saturate liquid olefins. The liquid produced from such hydrocracking and/or hydrotreating can be further sent to an aromatics extraction unit and/or a reforming unit to produce various aromatic hydrocarbons. Benzene can be recovered, and higher aromatics (e.g., $C_{7+}$ aromatics) can be further converted to benzene via disproportionation reactions. Benzene can be further alkylated with propylene to form cumene.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "X or more" means that the named component is present in an amount of the value X, and values which are more than X.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

For purposes of the disclosure herein, the term "amount" refers to a weight % of a given component in a particular composition, based upon the total weight of that particular composition (e.g., the total weight of all components present in that particular composition), unless otherwise indicated.

Figure 1B:
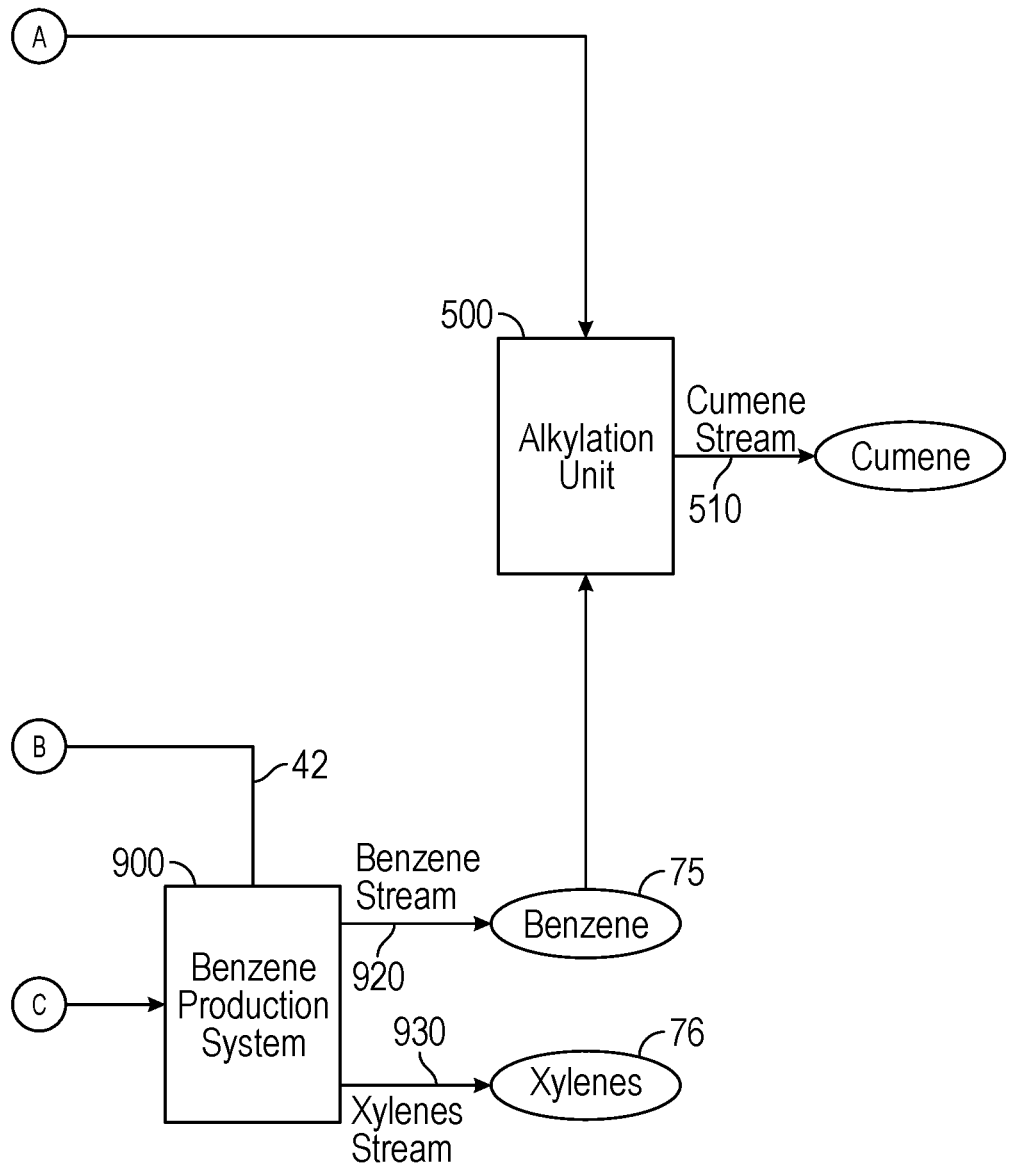

Processes for producing cumene, for example from mixed plastics (e.g., plastic waste) are described in more detail with reference to FIGS. 1A and 1B. Referring to FIGS. 1A and 1B, a cumene production system 1000 is disclosed. The cumene production system 1000 generally comprises a pyrolysis unit 100; a hydroprocessing unit or hydroprocessor 200; a first separating unit or first separator 300; an alkylation unit 500; a metathesis reactor 800; and a benzene production system 900. While the current disclosure will be discussed in detail in the context of a single pyrolysis unit; a single hydroprocessing unit; a single alkylation unit; a single metathesis reactor; and a single benzene production system, it should be understood that any suitable configurations for a cumene production system can be used, wherein any given configuration for a cumene production system can comprise 1, 2, or more pyrolysis units; 1, 2, or more hydroprocessing units; 1, 2, or more alkylation units; 1, 2, or more metathesis reactors; and 1, 2, or more benzene production systems.

A process for producing cumene can comprise a step of converting a plastic waste to a hydrocarbon liquid stream and a pyrolysis gas stream in a pyrolysis unit. The process can comprise introducing the waste plastics to a pyrolysis unit to produce a pyrolysis product, wherein the pyrolysis product comprises a gas phase and a liquid phase.

Mixed plastics (e.g., waste plastics) can be either placed in the pyrolysis unit 100 or fed to the pyrolysis unit 100 via waste plastic stream 110. In the pyrolysis unit 100, the waste plastic stream 110 is converted via pyrolysis to a pyrolysis product, wherein the pyrolysis product comprises a gas phase (e.g., pyrolysis gases, such as $C_1$ to $C_4$ gases, hydrogen ($H_2$), carbon monoxide (CO), carbon dioxide ($CO_2$), hydrochloric acid (HCl) gas, etc.) and a liquid phase (e.g., pyrolysis liquid).

Plastic waste which can be loaded into or fed to the pyrolysis unit 100 via waste plastic stream 110 may include post-consumer waste plastics, such as mixed plastic waste.

Mixed plastics can comprise non-chlorinated plastics (e.g., polyolefins, polyethylene, polypropylene, polystyrene, copolymers, etc.), chlorinated plastics (e.g., polyvinylchloride (PVC), polyvinylidene chloride (PVDC), etc.), and the like, or mixtures thereof. Generally, waste plastics comprise long chain molecules or polymer hydrocarbons. Waste plastics as disclosed herein also include used tires.

The pyrolysis unit 100 may be any suitable vessel configured to convert waste plastics into gas phase and liquid phase products (e.g., simultaneously). The vessel may be configured for gas phase, liquid phase, vapor-liquid phase, gas-solid phase, liquid-solid phase, or slurry phase operation. The vessel may contain one or more beds of inert material or pyrolysis catalyst comprising sand, zeolite, alumina, a catalytic cracking catalyst, or combinations thereof. Generally, the pyrolysis catalyst is capable of transferring heat to the components subjected to the pyrolysis process in the pyrolysis unit 100. Alternatively, the pyrolysis unit 100 can be operated without any catalyst (e.g., pure thermal pyrolysis). The pyrolysis unit 100 may be operated adiabatically, isothermally, nonadiabatically, non-isothermally, or combinations thereof. The pyrolysis reactions of this disclosure may be carried out in a single stage or in multiple stages. For example, the pyrolysis unit 100 can be two reactor vessels fluidly connected in series.

In a configuration where the pyrolysis unit 100 comprises two vessels, the pyrolysis process may be divided into a first stage which is performed in a first vessel and in a second stage fluidly connected downstream of the first stage which is performed in the second vessel. As will be appreciated by one of skill in the art, and with the help of this disclosure, the second stage may enhance the pyrolysis of an intermediate pyrolysis product stream flowing from the first stage into the second stage, to yield a pyrolysis product flowing from the second stage. In some configurations, the first stage may utilize thermal cracking of the waste plastics, and the second stage may utilize thermal or catalytic cracking of the waste plastics to yield the pyrolysis product flowing from the second stage. Alternatively, the first stage may utilize catalytic cracking of the waste plastics, and the second stage may utilize thermal or catalytic cracking of the waste plastics to yield the pyrolysis product flowing from the second stage.

In some configurations, the pyrolysis unit 100 may include one or more equipment configured to convert mixed plastics into gas phase and liquid phase products. The one or more equipment may or may not contain an inert material or pyrolysis catalyst as described above. Examples of such equipment include one or more of heated extruders, heated rotating kiln, heated tank-type reactors, packed bed reactors, bubbling fluidized bed reactors, circulating fluidized bed reactors, empty heated vessels, enclosed heated surfaces where plastic flows down along the wall and cracks, vessels surrounded by ovens or furnaces, or any other suitable equipment offering a heated surface to assist in cracking.

The pyrolysis unit 100 can be configured to pyrolyze (e.g., crack), and in some aspects (e.g., where hydrogen is added to the pyrolysis unit 100), additionally hydrogenate components of the waste plastic stream 110 fed to the pyrolysis unit 100. Examples of reactions which may occur in the pyrolysis unit 100 include, but are not limited to isomerization of one or more normal paraffins to one or more i-paraffins, selective ring opening of one or more cycloparaffins to one or more i-paraffins, cracking of long chain length molecules to short chain length molecules, removal of heteroatoms from heteroatom-containing hydrocarbons (e.g., dechlorination), hydrogenation of coke generated in the process, or combinations thereof.

In one or more configurations of the pyrolysis unit 100, a head space purge gas can be utilized in all or a portion of the pyrolysis stage(s) (conversion of waste plastics to a liquid phase and/or gas phase products) to enhance cracking of plastics, produce valuable products, provide a feed for steam cracking, or combinations thereof. The head space purge gas may include hydrogen ($H_2$), $C_1$ to $C_4$ hydrocarbon gases (e.g., alkanes, methane, ethane, propane, butane, isobutane), inert gases (e.g., nitrogen ($N_2$), argon, helium, steam), and the like, or combinations thereof. The use of a head space purge gas assists in the dechlorination in the pyrolysis unit 100, when the waste plastic comprises chlorinated plastics. The head space purge gas may be introduced to the pyrolysis unit 100 to aid in the removal of volatiles entrained in the melted mixed plastics present in the pyrolysis unit 100.

A hydrogen ($H_2$) containing stream can be added to the pyrolysis unit 100 to enrich the pyrolysis unit environment with $H_2$, assist in stripping entrapped hydrogen chloride in the pyrolysis unit, provide a local environment rich in hydrogen in the pyrolysis melt or liquid, or combinations thereof; for example via a $H_2$ containing stream fed directly to the pyrolysis unit independently of the waste plastic stream 110. In some aspects, $H_2$ can also be introduced along with stream 110 to the pyrolysis unit 100, with adequate safety measures incorporated for hydrogen handling with plastics feed.

The pyrolysis unit 100 may facilitate any reaction of the components of the waste plastic stream 110 in the presence of, or with, hydrogen. Reactions may occur such as the addition of hydrogen atoms to double bonds of unsaturated molecules (e.g., olefins), resulting in saturated molecules (e.g., paraffins, i-paraffins, naphthenes). Additionally or alternatively, reactions in the pyrolysis unit 100 may cause a rupture of a bond of an organic compound, with a subsequent reaction and/or replacement of a heteroatom with hydrogen.

The use of hydrogen in the pyrolysis unit 100 can have beneficial effects of i) reducing the coke as a result of cracking, ii) keeping the catalyst used (if any) in the process in an active condition, iii) improving removal of chloride from stream 110 such that the pyrolysis product from pyrolysis unit 100 is substantially dechlorinated with respect to waste plastic stream 110, which minimizes the chloride removal requirement in units downstream of the pyrolysis unit 100, iv) hydrogenating of olefins, v) reducing diolefins in pyrolysis product, vi) helping operate the pyrolysis unit 100 at reduced temperatures for same levels of conversion of waste plastic stream 110 in the pyrolysis unit 100, or combinations of i)-vi).

The pyrolysis processes in the pyrolysis unit 100 may be low severity or high severity. Low severity pyrolysis processes may occur at a temperature of less than about 450° C., alternatively 250° C. to 450° C., alternatively 275° C. to 425° C., or alternatively 300° C. to 400° C., and may produce pyrolysis oils rich in mono- and di-olefins as well as a significant amount of aromatics. High severity pyrolysis processes may occur at a temperature of equal to or greater than about 450° C., alternatively 450° C. to 750° C., alternatively 500° C. to 700° C., or alternatively 550° C. to 650° C., and may produce pyrolysis oils rich in aromatics, as well as more gas products (as compared with low severity pyrolysis). As will be appreciated by one of skill in the art, and with the help of this disclosure, when it is desired to produce more gases (e.g., propylene) during pyrolysis, a high severity pyrolysis process is preferred over a low severity pyrolysis process.

An example of a pyrolysis process for waste plastics is disclosed in U.S. Pat. No. 8,895,790, which is incorporated by reference in its entirety. Another example of a pyrolysis process is disclosed in International Publication No. WO 2016/009333 A1, and U.S. patent application Ser. No. 15/085,445 filed Mar. 30, 2016, each of which is incorporated by reference in its entirety.

A pyrolysis product can be recovered as an effluent from the pyrolysis unit 100 and conveyed (e.g., flowed, for example via pumping, gravity, pressure differential, etc.) to a pyrolysis separating unit. The pyrolysis product can be separated in the pyrolysis separating unit into a pyrolysis gas stream 120 and a hydrocarbon liquid stream 130, wherein the pyrolysis gas stream 120 comprises at least a portion of the gas phase of the pyrolysis product, and wherein the hydrocarbon liquid stream 130 comprises at least a portion of the liquid phase of the pyrolysis product. The pyrolysis separating unit may comprise any suitable gas-liquid separator, such as a vapor-liquid separator, oil-gas separators, gas-liquid separators, degassers, deliquizers, scrubbers, traps, flash drums, compressor suction drums, gravity separators, centrifugal separators, filter vane separators, mist eliminator pads, liquid-gas coalescers, distillation columns, and the like, or combinations thereof.

In some configurations, the pyrolysis separating unit can be a condenser which operates at conditions which condense a portion of the pyrolysis product into hydrocarbon liquids (e.g., liquid product) while leaving the hydrocarbon gases in the gas phase (e.g., gas product). A liquid product flows from the pyrolysis separating unit in hydrocarbon liquid stream 130, and a gas product flows from the pyrolysis separating unit in pyrolysis gas stream 120. The pyrolysis gas stream 120 can comprise $H_2$, $C_1$ to $C_4$ hydrocarbons, inert gases (e.g., nitrogen ($N_2$), argon, helium, steam, CO, $CO_2$), and the like, or combinations thereof.

The hydrocarbon liquid stream 130 can comprise paraffins, i-paraffins, olefins, naphthenes, aromatic compounds, organic chlorides, or combinations thereof. When the hydrocarbon liquid stream 130 comprises paraffins, i-paraffins, olefins, naphthenes, and aromatic compounds, the stream can be referred to as a PIONA stream; and when the hydrocarbon liquid stream 130 comprises paraffins, olefins, naphthenes, and aromatic compounds, the stream can be referred to as a PONA stream. In some aspects, the hydrocarbon liquid stream 130 can comprise a plastic pyrolysis oil and/or a tire pyrolysis oil.

As discussed herein, aspects of the processes disclosed herein contemplate hydrocracking of molecules, and in particular, heavy hydrocarbon molecules of the hydrocarbon liquid stream 130. As such, it is contemplated that at least a portion of the hydrocarbon liquid stream 130 comprises heavy hydrocarbon molecules (e.g., also referred to as heavy ends of pyrolysis oils). In an aspect, an amount of heavy hydrocarbon molecules in the hydrocarbon liquid stream 130 may be less than 10 wt. %, based on the total weight of the hydrocarbon liquid stream 130. Alternatively, the amount of the heavy hydrocarbon molecules in the hydrocarbon liquid stream 130 may be from 10 wt. % to 90 wt. %, based on the total weight of the hydrocarbon liquid stream 130. As will be described in more detail later herein, the heavy hydrocarbon molecules may include paraffins, i-paraffins, olefins, naphthenes, aromatic hydrocarbons, or combinations thereof. In some aspects, the heavy hydrocarbon molecules may include $C_{16}$ and larger hydrocarbons. Greater than 5, 10, 15, 20, 25, 30 wt. % or more of the heavy hydrocarbon molecules in the hydrocarbon liquid stream 130 is hydrocracked in the hydroprocessing unit 200.

Examples of paraffins which may be present in the hydrocarbon liquid stream 130 include, but are not limited to, $C_1$ to $C_{22}$ n-paraffins and i-paraffins. The paraffins can be present in the hydrocarbon liquid stream 130 in an amount of less than 10 wt. % based on the total weight of the hydrocarbon liquid stream 130. Alternatively, the paraffins can be present in the hydrocarbon liquid stream 130 in an amount of 10 wt. %, 20 wt. %, 30 wt. %, 40 wt. %, 50 wt. %, 60 wt. %, or more based on the total weight of the hydrocarbon liquid stream 130. While certain hydrocarbon liquid streams include paraffins of carbon numbers up to 22, the present disclosure is not limited to carbon number 22 as an upper end-point of the suitable range of paraffins, and the paraffins can include higher carbon numbers, e.g., 23, 24, 25, 26, 27, 28, 29, 30, 31, 32, 33, 34, 35, 36, 37, 38, 39, 40, and higher. In some aspects, at least a portion of the paraffins in the hydrocarbon liquid stream 130 comprises at least a portion of the heavy hydrocarbon molecules.

Examples of olefins which may be present in hydrocarbon liquid stream 130 include, but are not limited to, $C_2$ to $C_{10}$ olefins and combinations thereof. Where hydrogen is introduced to the pyrolysis unit 100, due to hydrogenation reactions in the pyrolysis unit 100, the olefins can be present in the hydrocarbon liquid stream 130 in an amount of less than 10 wt. %, based on the total weight of the hydrocarbon liquid stream 130. Alternatively, the olefins can be present in the hydrocarbon liquid stream 130 in an amount of 5 wt. %, 10 wt. %, 20 wt. %, 30 wt. %, 40 wt. %, or more based on the total weight of the hydrocarbon liquid stream 130. While certain hydrocarbon streams include olefins of carbon numbers up to 100, the present disclosure is not limited to carbon number 100 as an upper end-point of the suitable range of olefins, and the olefins can include higher carbon numbers, e.g., 11, 12, 13, 14, 15, 16, 17, 18, 19, 20, 21, 22, 23, 24, 25, 26, 27, 28, 29, 30, and higher. In some aspects, at least a portion of the one or more olefins in the hydrocarbon liquid stream 130 comprise at least a portion of the heavy hydrocarbon molecules. Alternatively, none of the heavy hydrocarbon molecules in the hydrocarbon liquid stream 130 are olefins.

In some aspects, the hydrocarbon liquid stream 130 comprises no olefins, e.g., the hydrocarbon liquid stream 130 is substantially free of olefins. In some aspects, the hydrocarbon liquid stream 130 comprises less than 1, 0.1, 0.01, or 0.001 wt. % olefins.

Examples of naphthenes which may be present in the hydrocarbon liquid stream 130 include, but are not limited to, cyclopentane, cyclohexane, cycloheptane, and cyclooctane. The naphthenes can be present in the hydrocarbon liquid stream 130 in an amount of less than 10 wt. %, based on the total weight of the hydrocarbon liquid stream 130. Alternatively, the naphthenes can be present in the hydrocarbon liquid stream 130 in an amount of 10 wt. %, 20 wt. %, 30 wt. %, 40 wt. %, or more based on the total weight of the hydrocarbon liquid stream 130. While certain hydrocarbon streams include naphthenes of carbon numbers up to 8, the present disclosure is not limited to carbon number 8 as an upper end-point of the suitable range of naphthenes, and the naphthenes can include higher carbon numbers, e.g., 9, 10, 11, 12, 13, 14, 15, 16, 17, 18, 19, 20, 21, 22, 23, 24, 25, 26, 27, 28, 29, 30, and higher. In some aspects, at least a portion of the naphthenes in the hydrocarbon liquid stream 130 comprises at least a portion of the heavy hydrocarbon molecules.

The hydrocarbon liquid stream 130 may comprise aromatic hydrocarbons with carbon numbers of 6, 7, 8, 9, 10, 11, 12, 13, 14, 15, 16, 17, 18, 19, 20, 21, 22, 23, 24, 25, 26, 27, 28, 29, 30, and higher. In an aspect, the aromatic hydrocarbons carbon number can be as high as 22. Nonlimiting examples of aromatic hydrocarbons suitable for use in the present disclosure as part of the hydrocarbon liquid stream 130 include benzene, toluene, xylenes, ethylbenzene, propylbenzenes, trimethylbenzenes, tetramethylbenzenes, butylbenzenes, dimethylnaphthalene, biphenyl, and the like, or combinations thereof. The aromatic hydrocarbons can be present in the hydrocarbon liquid stream 130 in an amount of 5 wt. %, 10 wt. %, 15 wt. %, 20 wt. %, 25 wt. %, 30 wt. %, 35 wt. %, 40 wt. %, 50 wt. %, 60 wt. %, or more based on the total weight of the hydrocarbon liquid stream 130. In some aspects, at least a portion of the aromatic hydrocarbons in the hydrocarbon liquid stream 130 comprises at least a portion of the heavy hydrocarbon molecules.

A process for producing cumene can comprise a step of contacting at least a portion of the hydrocarbon liquid stream 130 with a hydroprocessing catalyst in the presence of hydrogen in the hydroprocessing unit 200 to yield a hydrocarbon product stream 210 and a first gas stream 220, wherein the hydrocarbon product stream 210 comprises $C_5+$ hydrocarbons. The first gas stream 220 can comprise $H_2$, $C_1$ to $C_4$ hydrocarbons, inert gases (e.g., nitrogen ($N_2$), argon, helium, steam, CO, $CO_2$), and the like, or combinations thereof.

The hydroprocessing unit 200 can be any suitable hydroprocessing reactor, such as a hydrocracker, a catalytic cracker operated in hydropyrolysis mode, a fluid catalytic cracker operated in hydropyrolysis mode, a hydrotreater, and the like, or combinations thereof. The hydroprocessing unit 200 is configured to hydrocrack long chain molecules (e.g., heavy hydrocarbon molecules contained in the hydrocarbon liquid stream 130), hydrogenate and dechlorinate (where stream 130 contains chloride) components of the hydrocarbon liquid stream 130 fed to the hydroprocessing unit 200. In the hydroprocessing unit 200, the hydrocarbon liquid stream 130 is contacted with a hydroprocessing catalyst in the presence of hydrogen to yield the hydrocarbon product stream 210. It is contemplated that the hydrocarbon liquid stream 130 may be contacted with the hydroprocessing catalyst in upward flow, downward flow, radial flow, or combinations thereof, with or without a staged addition of hydrocarbon liquid stream 130, a $H_2$ stream, or combinations thereof.

The hydroprocessing unit 200 may be any vessel configured to contain the hydroprocessing catalyst disclosed herein. The vessel may be configured for gas phase, liquid phase, vapor-liquid phase, gas-liquid-solid phase, or slurry phase operation. The hydroprocessing unit 200 may include one or more beds of the hydroprocessing catalyst configured as a fixed bed, a fluidized bed, a moving bed, an ebullated bed, a slurry bed, or combinations thereof. The hydroprocessing unit 200 may be operated adiabatically, isothermally, nonadiabatically, non-isothermally, or combinations thereof. In an aspect, the hydroprocessing unit 200 may comprise one or more vessels.

The hydroprocessing unit 200 may facilitate any reaction of the components of the hydrocarbon liquid stream 130 in the presence of, or with, hydrogen. Reactions may occur as the addition of hydrogen atoms to double bonds of unsaturated molecules (e.g., olefins, aromatic compounds), resulting in saturated molecules (e.g., paraffins, i-paraffins, naphthenes). Additionally, reactions in the hydroprocessing unit 200 may cause a rupture of a bond of an organic compound, resulting in "cracking" of a hydrocarbon molecule into two or more smaller hydrocarbon molecules, or resulting in a subsequent reaction and/or replacement of a heteroatom with hydrogen. Examples of reactions which may occur in the hydroprocessing unit 200 include, but are not limited to, the hydrogenation of olefins, removal of heteroatoms from heteroatom-containing hydrocarbons (e.g., dechlorination), hydrocracking of large paraffins or i-paraffins to smaller hydrocarbon molecules, hydrocracking of aromatic hydrocarbons to smaller cyclic or acyclic hydrocarbons, conversion of one or more aromatic compounds to one or more cycloparaffins, isomerization of one or more normal paraffins to one or more i-paraffins, selective ring opening of one or more cycloparaffins to one or more i-paraffins, or combinations thereof.

In an aspect, contacting the hydrocarbon liquid stream 130 with the hydroprocessing catalyst in the presence of hydrogen yields $C_1$ to $C_4$ gases and $C_5+$ ($C_5$ and heavier) liquid hydrocarbons. When the waste plastic stream 110 contains chloride, it is contemplated that dechlorination using the hydroprocessing catalyst as described herein can be performed in the hydroprocessing unit 200 without the use of chlorine sorbents, without addition of $Na_2CO_3$ in an effective amount to function as a dechlorinating agent, or both.

The hydroprocessing catalyst may be any catalyst used for hydrogenation (e.g., saturation) of olefins and aromatic hydrocarbons (e.g., a commercially available hydrotreating catalyst). The hydroprocessing catalyst can comprise a cobalt and molybdenum catalyst (Co—Mo catalyst) on an alumina support, a nickel and molybdenum catalyst (Ni—Mo catalyst) on an alumina support, a tungsten and molybdenum catalyst (W—Mo catalyst) on an alumina support, cobalt and molybdenum oxides on an alumina support, nickel and molybdenum oxides on an alumina support, tungsten and molybdenum oxides on an alumina support, cobalt and molybdenum sulphides on an alumina support, nickel and molybdenum sulphides on an alumina support, tungsten and molybdenum sulphides on an alumina support, a zeolite comprising one or more metals, and the like, or combinations thereof. Other catalysts suitable for use as the hydroprocessing catalyst may include platinum and palladium catalyst (Pt—Pd catalyst) on an alumina support, nickel sulphides suitable for slurry processing, molybdenum sulphides suitable for slurry processing, and the like, or combinations thereof. The zeolites can comprise ZSM-5, ZSM-11, Y, high-silica Y, USY, and the like, or combinations thereof. Each metal of the one or more metals of the zeolite can be independently selected from the group consisting of cobalt, molybdenum, tungsten, nickel, titanium, copper, magnesium, tin, iron, zinc, tungsten, vanadium, gallium, calcium, manganese, ruthenium and rhenium.

In configurations where the hydrocarbon liquid stream 130 comprises one or more sulphides and one or more chloride compounds, contacting the hydrocarbon liquid stream 130 with the hydroprocessing catalyst acts to activate the hydroprocessing catalyst by sulphiding and to acidify the hydroprocessing catalyst by chlorinating. Continuously contacting the hydroprocessing catalyst with the hydrocarbon liquid stream 130 containing one or more sulphides, one or more chloride compounds, or both, may maintain catalyst activity on a continuous basis. For purposes of the disclosure herein, the term "catalyst activity" or "catalytic activity" with respect to the hydroprocessing catalyst refers to the ability of the hydroprocessing catalyst to catalyze hydroprocessing reactions, such as hydrocracking reactions, hydrodechlorination reactions, etc.

A hydrogen stream can be added to the hydroprocessing unit 200 to enrich the hydroprocessing unit environment with $H_2$, for example via a stream fed directly to the hydroprocessing unit independently of the hydrocarbon liquid stream 130. Additionally or alternatively, a $H_2$ containing stream can be added to the hydrocarbon liquid stream 130 before entering the hydroprocessing unit 200. The rate of hydrogen addition to the hydroprocessing unit 200 is generally sufficient to achieve the hydrogen to hydrocarbon ratios disclosed herein.

The disclosed hydroprocessing unit 200 may operate at various process conditions. For example, contacting the hydrocarbon liquid stream 130 with the hydroprocessing catalyst in the presence of hydrogen may occur in the hydroprocessing unit 200 at a temperature of from 250° C. to 600° C.; alternatively, 275° C. to 550° C.; or alternatively, 300° C. to 500° C. The temperature in the hydroprocessing unit 200 can be attained by using a feed (e.g., hydrocarbon liquid stream 130) pre-heating furnace and/or feed-hydroprocessing unit effluent heat exchangers. Contacting the hydrocarbon liquid stream 130 with the hydroprocessing catalyst in the presence of hydrogen may occur in the hydroprocessing unit 200 at a pressure of 1 barg to 200 barg, alternatively, 10 barg to 150 barg, or alternatively, 20 barg to 60 barg. Contacting the hydrocarbon liquid stream 130 with the hydroprocessing catalyst in the presence of hydrogen may occur in the hydroprocessing unit 200 at a weight hourly space velocity (WHSV) of between 0.1 $hr^{-1}$ to 10 $hr^{-1}$; or alternatively, 1 $hr^{-1}$ to 3 $hr^{-1}$. Contacting the hydrocarbon liquid stream 130 with the hydroprocessing catalyst in the presence of hydrogen may occur in the hydroprocessing unit 200 at a hydrogen to hydrocarbon ($H_2$/HC) flow ratio of from 10 NL/L to 3,000 NL/L; or alternatively, from 200 NL/L to 800 NL/L.

In some configurations, the hydroprocessing unit 200 can be a mild hydrocracking unit, such as a mild hydrocracker used in refining operations, wherein the hydroprocessing unit 200 can operate at pressures of up to 100 barg and at temperatures of up to 430° C. As will be appreciated by one of skill in the art, and with the help of this disclosure, the hydroprocessing unit 200 could operate at lower pressures to economize on hydrogen consumption and to preserve mono-ring aromatics (and only saturate di- and poly-aromatics, and olefins). Generally, mild hydrocracking units can saturate liquid olefins introduced to the mild hydrocracking unit, as well as reduce the heavies by selective cracking and hydrogenation, such that at least a portion of the mono-ring aromatics can be preserved. As will be appreciated by one of skill in the art, and with the help of this disclosure, since plastic pyrolysis oils are rich in hydrogen content compared to petroleum residues, it is possible to carry out the hydroprocessing at lower pressures of less than 100 barg. Further, as will be appreciated by one of skill in the art, and with the help of this disclosure, higher pressures of more than 100 barg can also be used with plastic pyrolysis oils.

In some aspects, the hydroprocessing unit 200 can further comprise a hydrodealkylating unit, wherein the hydrodealkylating unit can comprise a hydrodealkylating catalyst. The hydrodealkylating unit can be any suitable hydroprocessing reactor, such as a hydrocracker, a catalytic cracker operated in hydropyrolysis mode, a fluid catalytic cracker operated in hydropyrolysis mode, a hydrotreater, a hydrodealkylating reactor, and the like, or combinations thereof. The hydrodealkylating unit can be configured to hydrodealkylate, and in some configurations, additionally hydrocrack, dechlorinate and hydrogenate components of the hydrocarbon liquid stream 130.

The hydrodealkylating unit may be any vessel configured to contain the hydrodealkylating catalyst disclosed herein. The vessel may be configured for gas phase, liquid phase, vapor-liquid phase, gas-solid phase, gas-liquid-solid phase, or slurry phase operation. The hydrodealkylating unit may include one or more beds of the hydrodealkylating catalyst configured as a fixed bed, a fluidized bed, a moving bed, an ebullated bed, a slurry bed, or combinations thereof. The hydrodealkylating unit may be operated adiabatically, isothermally, nonadiabatically, non-isothermally, or combinations thereof. In an aspect, the hydrodealkylating unit may comprise one or more vessels.

The hydrodealkylating unit may facilitate any suitable reaction of the components of the hydrocarbon liquid stream 130 in the presence of, or with, hydrogen. Reactions in the hydrodealkylating unit include a hydrodealkylation reaction of $C_9$+ aromatic hydrocarbons, wherein the $C_9$+ aromatic hydrocarbons in the presence of hydrogen form lower molecular weight aromatic hydrocarbons (e.g., $C_{6-8}$ aromatic hydrocarbons) and alkanes. For example, trimethylbenzenes can undergo a hydrodealkylation reaction to produce xylenes and methane. Other reactions may occur in the hydrodealkylating unit, such as the addition of hydrogen atoms to double bonds of unsaturated molecules (e.g., olefins, aromatic compounds), resulting in saturated molecules (e.g., paraffins, i-paraffins, naphthenes). Additionally, reactions in the hydrodealkylating unit may cause a rupture of a bond of an organic compound, resulting in "cracking" of a hydrocarbon molecule into two or more smaller hydrocarbon molecules, or resulting in a subsequent reaction and/or replacement of a heteroatom with hydrogen. Examples of reactions which may occur in the hydrodealkylating unit include, but are not limited to, hydrodealkylation of $C_9$+ aromatic hydrocarbons, the hydrogenation of olefins, removal of heteroatoms from heteroatom-containing hydrocarbons (e.g., dechlorination), hydrocracking of large paraffins or i-paraffins to smaller hydrocarbon molecules, hydrocracking of aromatic hydrocarbons to smaller cyclic or acyclic hydrocarbons, conversion of one or more aromatic compounds to one or more cycloparaffins, isomerization of one or more normal paraffins to one or more i-paraffins, selective ring opening of one or more cycloparaffins to one or more i-paraffins, or combinations thereof.

The hydrodealkylating catalyst may be any suitable catalyst used for hydrogenation (e.g., saturation) of olefins and aromatic hydrocarbons (e.g., a commercially available hydrotreating catalyst), such as the catalysts described herein for the hydroprocessing catalyst. Additionally, the hydrodealkylating catalyst may be any suitable hydrodealkylation catalyst (e.g., a commercially available hydrodealkylation catalyst), such as chromium oxides on an alumina support, chromium oxides on a silica support, molybdenum oxides on an alumina support, molybdenum oxides on a silica support, platinum on an alumina support, platinum on a silica support, platinum oxides on an alumina support, platinum oxides on a silica support, and the like, or combinations thereof.

The hydrocarbon product stream 210 comprises $C_5$+ liquid hydrocarbons, wherein the $C_5$+ liquid hydrocarbons comprise heavy hydrocarbon molecules. An amount of heavy hydrocarbon molecules in the hydrocarbon product stream 210 is less than an amount of heavy hydrocarbon molecules in the hydrocarbon liquid stream 130 due to hydrocracking of at least a portion of heavy hydrocarbon molecules from the hydrocarbon liquid stream during the step of contacting the hydrocarbon liquid stream 130 with a hydroprocessing catalyst in the presence of hydrogen in the hydroprocessing unit 200.

In some aspects, the hydrocarbon product stream 210 can comprise equal to or greater than about 90 wt. %, alternatively equal to or greater than about 92.5 wt. %, or alternatively equal to or greater than about 95 wt. % $C_{10}$- hydrocarbons, based on the total weight of the hydrocarbon product stream 210. As will be appreciated by one of skill in the art, and with the help of this disclosure, the conditions inside the hydroprocessing unit 200 can be such that the produced hydrocarbon product comprises mostly $C_{10}$- hydrocarbons.

In other aspects, the hydrocarbon product stream 210 can comprise equal to or greater than about 95 wt. %, alternatively equal to or greater than about 96 wt. %, or alternatively equal to or greater than about 97.5 wt. % $C_8$- hydrocarbons (e.g., $C_5$ to $C_8$ hydrocarbons), based on the total weight of the hydrocarbon product stream 210. As will be appreciated by one of skill in the art, and with the help of this disclosure, the conditions inside the hydroprocessing unit 200 can be such that the produced hydrocarbon product comprises mostly $C_8$- hydrocarbons (e.g., $C_5$ to $C_8$ hydrocarbons).

The hydrocarbon product stream 210 can be characterized by an olefin content that is lower than an olefin content of the hydrocarbon liquid stream 130. In some aspects, the hydrocarbon product stream 210 can be characterized by an olefin content of less than about 1, 0.1, 0.01, or 0.001 wt. % olefins, based on the total weight of the hydrocarbon product stream 210.

The hydrocarbon product stream 210 can be characterized by a boiling point that is lower than the boiling point of the hydrocarbon liquid stream 130. In an aspect, equal to or greater than about 97 wt. %, alternatively 98 wt. %, or alternatively 99.9 wt. % of the hydrocarbon product stream 210 is characterized by a boiling point of less than about 370° C., or alternatively less than about 350° C. In some aspects, the hydrocarbon product stream 210 is characterized by a boiling point of less than about 370° C.

The hydrocarbon product stream 210 can be characterized by a chloride content that is lower than a chloride content of the hydrocarbon liquid stream 130, wherein a decrease in chloride content results from dehydrochlorination of the hydrocarbon liquid stream 130 during the step of contacting the hydrocarbon liquid stream 130 with a hydroprocessing catalyst in the presence of hydrogen in the hydroprocessing unit 200. The hydrocarbon product stream 210 can comprise one or more chloride compounds in an amount of less than about 10 parts per million weight (ppmw) chloride, alternatively less than about 5 ppmw chloride, or alternatively less than about 3 ppmw chloride, based on the total weight of the hydrocarbon product stream 210.

A process for producing cumene can comprise a step of feeding at least a portion of the hydrocarbon product stream 210 to the benzene production system 900 to produce a benzene stream 920, a xylenes stream 930, and a second gas stream 42, wherein the benzene stream 920 comprises benzene 75, and wherein the xylenes stream 930 comprises xylenes 76.

Figure 2A:
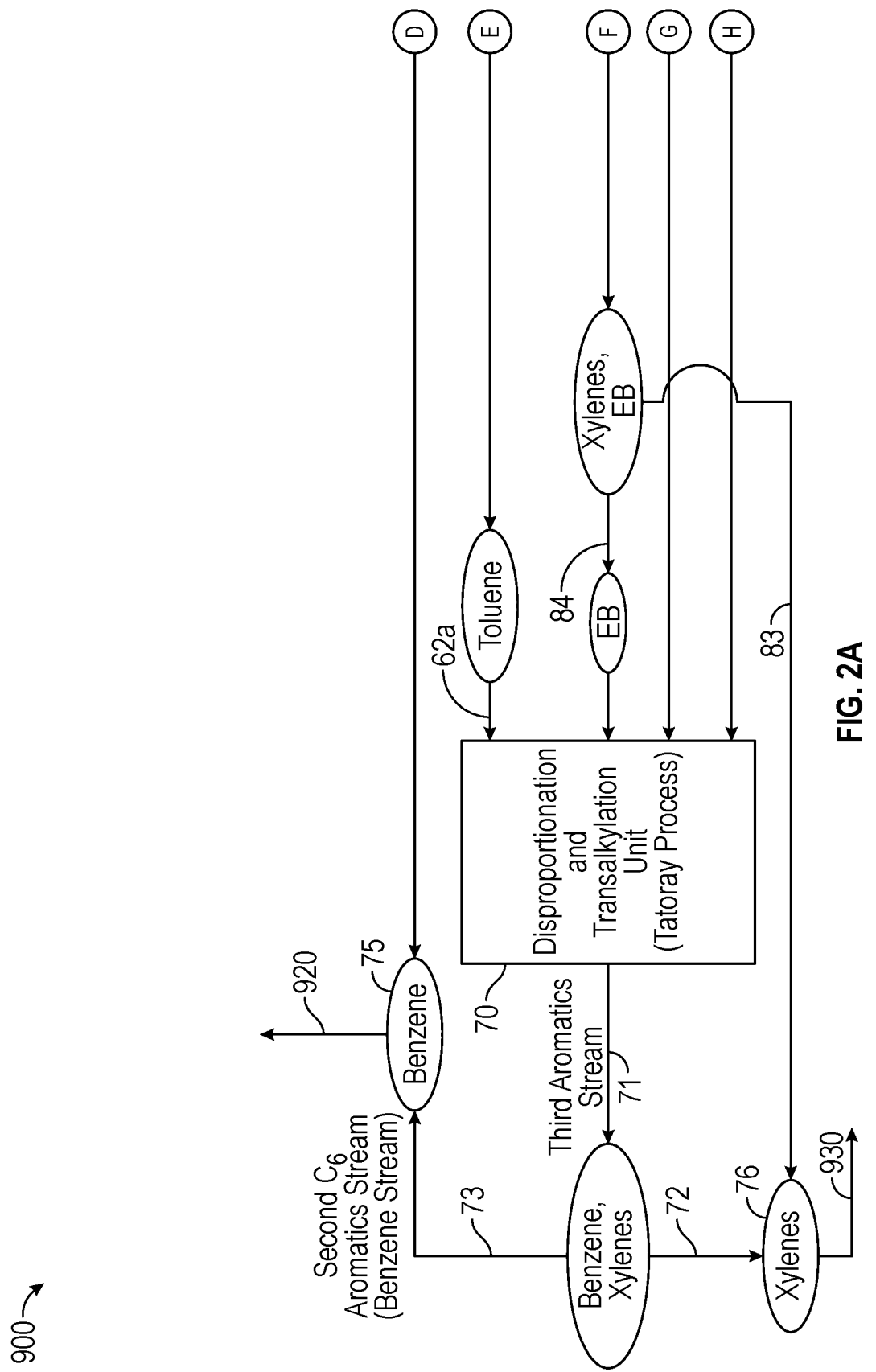
FIGS. 2A and 2B display a configuration of a system for producing benzene.
Figure 2B:
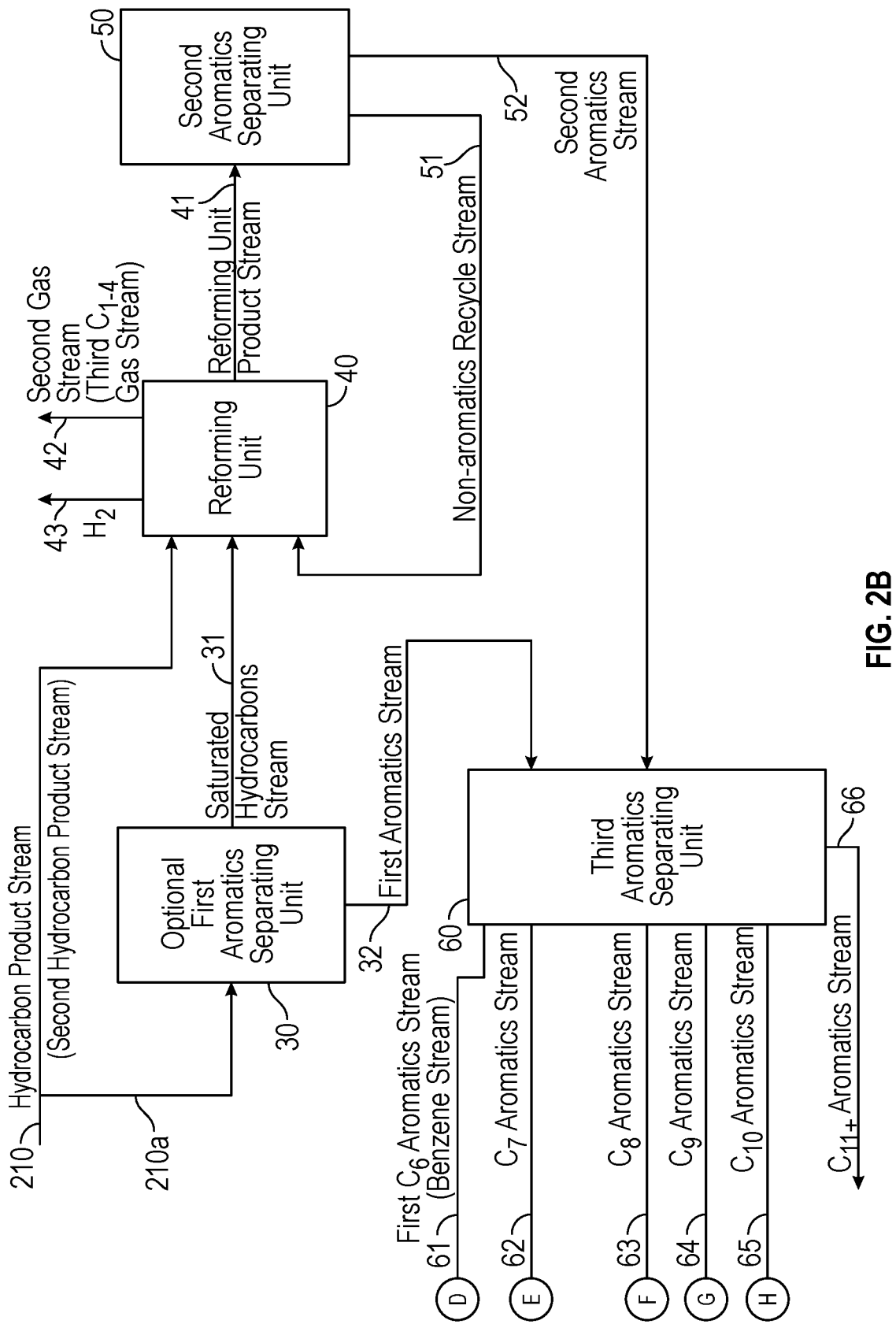

Referring to FIGS. 2A and 2B, the benzene production system 900 is disclosed. The benzene production system 900 generally comprises an optional first aromatics separating unit or first aromatics separator 30; a reforming unit 40; a second aromatics separating unit or second aromatics separator 50; a third aromatics separating unit or third aromatics separator 60; and a disproportionation and transalkylation unit (e.g., Tatoray unit) 70.

A process for producing cumene can comprise a step of optionally introducing at least a portion 210a of the hydrocarbon product stream to the first aromatics separating unit 30 to produce a saturated hydrocarbons stream 31 and a first aromatics stream 32, wherein the saturated hydrocarbons stream 31 comprises $C_5$+ saturated hydrocarbons, and wherein the first aromatics stream 32 comprises $C_6$+ aromatic hydrocarbons. As will be appreciated by one of skill in the art, and with the help of this disclosure, the $C_{5+}$ saturated hydrocarbons of the saturated hydrocarbons stream 31 (i) exclude $C_{6+}$ aromatic hydrocarbons; (ii) exclude $C_{5+}$ olefins; and (iii) include $C_{5+}$ paraffins, isoparaffins and naphthenes. The first aromatics stream 32 comprises $C_6$ aromatic hydrocarbons, $C_7$ aromatic hydrocarbons, $C_8$ aromatic hydrocarbons, $C_9$ aromatic hydrocarbons, $C_{10}$ aromatic hydrocarbons, and combinations thereof.

The first aromatics separating unit 30 can comprise any suitable separating unit that is configured to separate the hydrocarbon product stream 210 into the saturated hydrocarbons stream 31 and the first aromatics stream 32. For example, the first aromatics separating unit 30 can employ selective adsorption, selective absorption, extractive distillation, and the like, or combinations thereof.

A process for producing cumene can comprise a step of feeding at least a portion of the hydrocarbon product stream 210 and/or at least a portion of the saturated hydrocarbons stream 31 to the reforming unit 40 to produce a reforming unit product stream 41, a second gas stream 42, and a hydrogen stream 43, wherein the reforming unit 40 comprises a reforming catalyst. In an aspect, at least a portion of the hydrogen stream 43 can be recycled to the hydroprocessing unit 200 and/or the pyrolysis unit 100. The second gas stream 42 can comprise $H_2$ and $C_1$ to $C_4$ hydrocarbons.

The reforming unit 40 can comprise any suitable aromatizing unit, such as a continuous catalytic reformer (CCR), a semi-regenerative reformer, an AROMAX unit, and the like, or combinations thereof. Aromatizing units generally produce aromatics from naphthenes and paraffins, as a source of specific aromatic compounds. In some aspects, the feed to the reforming unit 40 (e.g., hydrocarbon product stream 210 and/or saturated hydrocarbons stream 31) can be generally restricted to $C_6$ through $C_{10}$ compounds, or alternatively $C_6$ through $C_8$ compounds to maximize the production of $C_6$ to $C_8$ aromatic hydrocarbons, such as benzene, toluene, and xylenes. In an aspect, an amount of $C_6$ to $C_8$ aromatic hydrocarbons in the reforming unit product stream 41 is greater than an amount of $C_6$ to $C_8$ aromatic hydrocarbons in the hydrocarbon product stream 210 and/or saturated hydrocarbons stream 31.

The reforming unit 40 may facilitate any suitable reaction of the components of the hydrocarbon product stream 210 and/or saturated hydrocarbons stream 31 in the presence of the reforming catalyst. Reactions in the reforming unit 40 include dehydrogenation of naphthenes to aromatics; isomerisation of paraffins and naphthenes; dehydrocyclization of paraffins to aromatics; and the like; or combinations thereof.

The reforming catalyst may be any suitable catalyst used for hydrocarbon aromatization. The reforming catalyst can be monometallic (e.g., Pt), bimetallic (Pt, Re), multimetallic (e.g., Pt, Re, Pd, Ni, etc.). The metals of the reforming catalyst generally promote dehydrogenation and hydrogenation, as well as contribute to dehydrocyclization and isomerization. The reforming catalyst can have acid activity (e.g., halogens/silica incorporated in alumina base). The acid activity promotes isomerization, the initial step in hydrocracking, as well as participation in paraffin dehydrocyclization.

The reforming unit product stream 41 can comprise equal to or greater than about 60 wt. %, 70 wt. %, or 80 wt. % aromatic hydrocarbons, and less than about 40 wt. %, 30 wt. %, or 20 wt. % non-aromatic hydrocarbons (e.g., paraffins, iso-paraffins, naphthenes).

A process for producing cumene can comprise a step of introducing at least a portion of the reforming unit product stream 41 to the second aromatics separating unit 50 to produce a non-aromatics recycle stream 51 and a second aromatics stream 52, wherein the second aromatics stream 52 comprises $C_6$+ aromatic hydrocarbons. As will be appreciated by one of skill in the art, and with the help of this disclosure, the non-aromatics recycle stream 51 (i) excludes $C_{6+}$ aromatic hydrocarbons; and (ii) includes $C_{5+}$ paraffins, iso-paraffins and naphthenes. The second aromatics stream 52 comprises $C_6$ aromatic hydrocarbons, $C_7$ aromatic hydrocarbons, $C_8$ aromatic hydrocarbons, $C_9$ aromatic hydrocarbons, $C_{10}$ aromatic hydrocarbons, and combinations thereof.

The second aromatics separating unit 50 can comprise any suitable separating unit that is configured to separate the reforming unit product stream 41 into the non-aromatics recycle stream 51 and the second aromatics stream 52. For example, the second aromatics separating unit 50 can employ selective adsorption, selective absorption, extractive distillation, and the like, or combinations thereof.

In some aspects, at least a portion of the non-aromatics recycle stream 51 can be recycled to the reforming unit 40. In other aspects, at least a portion of the non-aromatics recycle stream 51 can be recycled to the pyrolysis unit 100 and/or the hydroprocessing unit 200. As will be appreciated by one of skill in the art, and with the help of this disclosure, when the desired products are liquid aromatics, it is preferable to recycle the non-aromatics recycle stream 51 to the reforming unit 40. Further, as will be appreciated by one of skill in the art, and with the help of this disclosure, when it is desired to maximize gas products, such as pyrolysis gas stream 120 and/or first gas stream 220, it is preferable to recycle the non-aromatics recycle stream 51 to the pyrolysis unit 100 and/or the hydroprocessing unit 200, respectively.

A process for producing cumene can comprise a step of introducing at least a portion of the first aromatics stream 32 and/or at least a portion of the second aromatics stream 52 to the third aromatics separating unit 60 to produce a first $C_6$ aromatics stream (e.g., a benzene stream) 61, a $C_7$ aromatics stream 62, a $C_8$ aromatics stream 63, a $C_9$ aromatics stream 64, a $C_{10}$ aromatics stream 65, and a $C_{11}$+ aromatics stream 66, wherein the benzene stream 61 comprises benzene 75, wherein the $C_7$ aromatics stream 62 comprises toluene, and wherein the $C_8$ aromatics stream 63 comprises xylenes and ethylbenzene (EB). The $C_9$ aromatics stream 64 can comprise trimethylbenzene, methylethylbenzene, propylbenzene, and the like, or combinations thereof. The $C_{10}$ aromatics stream 65 can comprise tetramethylbenzene, diethylbenzene, dimethylethylebenzene, methylpropylbenzene, and the like, or combinations thereof.

The third aromatics separating unit 60 can comprise any suitable separating unit that is configured to separate the first aromatics stream 32 and/or the second aromatics stream 52 into its components (e.g., streams 61, 62, 63, 64, 65, and 66). In some aspects, the third aromatics separating unit 60 can comprise one or more distillation columns. Generally, the one or more distillation columns can separate components of the first aromatics stream 32 and/or the second aromatics stream 52 based on their boiling points.

In some aspects, at least a portion of the $C_{11}$+ aromatics stream 66 can be conveyed to the hydroprocessing unit 200. In other aspects, at least a portion of the $C_{11}$+ aromatics stream can be conveyed to the pyrolysis unit 100. The $C_{11}$+ aromatics stream 66 can comprise methylbutylbenzene, diethylmethylbenzene, pentamethylbenzene, 1-methylnaphthalaene, 2-methylnaphthalaene, 2-ethylnaphthalaene, dimethylnaphthalaene, and the like, or combinations thereof.

The process for producing cumene can further comprise recovering at least a portion of the xylenes from the $C_8$ aromatics stream 63. In some aspects, the process for producing cumene can further comprise separating the $C_8$ aromatics stream 63 into a first xylenes stream 83 and an EB stream 84, for example via extractive distillation, fractional crystallization, selective adsorption using molecular sieves, or combinations thereof. The first xylenes stream 83 can comprise xylenes 76 (e.g., p-xylene). The EB stream 84 can comprise EB, and o-xylene and m-xylene.

In some aspects, at least a portion of the EB stream 84 can be further isomerized to produce xylenes (e.g., p-xylene) in an isomerizing unit, wherein the isomerizing unit comprises an isomerization catalyst. The isomerization catalyst can comprise an acid catalyst, for example a bifunctional catalyst. As will be appreciated by one of skill in the art, and with the help of this disclosure, bifunctional isomerization catalysts are more stable to deactivation by coking than monofunctional isomerization catalysts. Bifunctional isomerization catalysts can comprise a zeolite (e.g., ZSM-5, mordenite) and a noble metal (e.g., Pt) supported on alumina or silica-alumina. Hydrogen can be introduced to the isomerizing unit to avoid catalyst coking.

In other aspects, at least a portion of the EB stream 84 can be further dealkylated to produce benzene in a dealkylation unit, wherein the dealkylation unit comprises a dealkylation catalyst. The main product of EB dealkylation is benzene (e.g., benzene 75), and the dealkylation catalyst generally comprises a metal loaded zeolite, wherein the metal can be Pt, Pd, Ni, Mo, etc.

A process for producing cumene can comprise a step of contacting at least a portion 62a of the $C_7$ aromatics stream, at least a portion of the $C_9$ aromatics stream 64, at least a portion of the $C_{10}$ aromatics stream 65, at least a portion of the EB stream 84, or combinations thereof with a disproportionation and transalkylation catalyst in the presence of hydrogen in the disproportionation and transalkylation unit 70 to yield a third aromatics stream 71, wherein the third aromatics stream 71 comprises benzene and xylenes. In an aspect, the disproportionation and transalkylation unit 70 comprises a Tatoray unit, i.e., a disproportionation and transalkylation unit housing a Tatoray process (e.g., disproportionation and transalkylation process).

A disproportionation and transalkylation process (e.g., Tatoray process) is generally used to selectively convert toluene and $C_9$ aromatics, and in some cases $C_{10}$ aromatics, into benzene and xylenes, for example to maximize xylenes (e.g., para-xylene) production. The Tatoray process produces mixed xylenes from toluene and heavy aromatics. As will be appreciated by one of skill in the art, and with the help of this disclosure, a Tatoray process generally shifts chemical equilibrium from benzene production to xylenes production.

The two major reactions in a Tatoray process are disproportionation and transalkylation. For purposes of the disclosure herein, the conversion of toluene into benzene and xylenes can be referred to as "disproportionation" (e.g., toluene disproportionation). Further, for purposes of the disclosure herein, the term "transalkylation" refers to the conversion of a mixture of toluene and $C_9$ aromatics, and in some cases $C_{10}$ aromatics into xylenes. Tatoray process reactions are conducted in a hydrogen atmosphere to minimize coke formation on catalyst. Because there is negligible ring destruction in the Tatoray process, there is very little hydrogen consumption. Most of the hydrogen consumption in a Tatoray process can be attributed to the cracking of the non-aromatic impurities in the feed to the Tatoray unit (e.g., disproportionation and transalkylation unit 70). Generally, reaction conditions in a Tatoray process can include temperatures of from about 350° C. to about 525° C.; pressures of from about 10 atm to about 50 atm; and hydrocarbon to hydrogen molar ratios of from about 5:1 to about 20:1.

In an aspect, the process for producing cumene can further comprise conveying at least a portion of the hydrogen stream 43 to the disproportionation and transalkylation unit 70.

Nonlimiting examples of disproportionation and transalkylation catalysts suitable for use in the present disclosure include a zeolite; a ZSM-5 characterized by Si/Al ratio of equal to or greater than about 10; a metal loaded ZSM-5, wherein the metal comprises platinum, molybdenum, magnesium, rhenium, or combinations thereof; mordenite; a bismuth oxide loaded mordenite; beta zeolite; MCM-22; and the like; or combinations thereof.

The process for producing cumene can further comprise recovering at least a portion of benzene from the third aromatics stream 71. In an aspect, the third aromatics stream 71 can be further separated into a second $C_6$ aromatics stream (e.g., benzene stream) 73 comprising benzene 75 and a second xylenes stream 72 comprising xylenes 76, for example via distillation. In some aspects, the second xylenes stream comprises p-xylene, o-xylene and m-xylene. The second xylenes stream can be further separated into a p-xylene fraction, and an o-xylene and m-xylene fraction, for example via extractive distillation, fractional crystallization, selective adsorption using molecular sieves, or combinations thereof.

For purposes of the disclosure herein, benzene stream 920 (as depicted in FIG. 1B) can comprise the first $C_6$ aromatics stream 61 and/or the second $C_6$ aromatics stream 73 (as depicted in FIGS. 2A and 2B), as well as any other benzene recovered from the benzene production system 900, for example benzene produced by EB dealkylation. Further, for purposes of the disclosure herein, xylenes stream 930 (as depicted in FIG. 1B) can comprise the first xylenes stream 83 and/or the second xylenes stream 72 (as depicted in FIG. 2A), as well as any other xylene recovered from the benzene production system 900.

A process for producing cumene can comprise a step of introducing at least a portion of the pyrolysis gas stream 120, at least a portion of the first gas stream 220, at least a portion of the second gas stream 42, or combinations thereof to the first separating unit 300 to produce a first propylene stream 310, a first $C_2$ and $C_4$ unsaturated stream 320, and a saturated gas stream 330, wherein the first propylene stream 310 comprises propylene, wherein the first $C_2$ and $C_4$ unsaturated stream 320 comprises ethylene and butylenes, and wherein the saturated gas stream 330 comprises hydrogen and $C_1$ to $C_4$ saturated hydrocarbons, as well as CO and $CO_2$.

The first separating unit 300 can be any suitable separating unit that is configured to separate the pyrolysis gas stream 120 and/or the first gas stream 220 into the first propylene stream 310, the first $C_2$ and $C_4$ unsaturated stream 320, and the saturated gas stream 330. For example, the first separating unit 300 can employ distillation columns, cryogenic distillation columns, extractive distillation columns, selective adsorption units, selective absorption units, and the like, or combinations thereof.

A process for producing cumene can comprise a step of feeding at least a portion of the first $C_2$ and $C_4$ unsaturated stream 320 to the metathesis reactor 800 to produce a second propylene stream 810, wherein the metathesis reactor 800 comprises a metathesis catalyst, and wherein the second propylene stream 810 comprises propylene. Generally, olefin metathesis refers to a reaction that entails redistribution of olefin fragments by scission and regeneration of carbon-carbon double bonds, a process also known as transalkylidenation. Olefins Conversion Technology (OCT) of Lummus Technology provides an example of olefin metathesis for the conversion of ethylene and butylenes to propylene.

The metathesis reactor 800 can comprise any suitable metathesis reactor, such as a continuous flow reactor, a batch reactor, a fixed bed reactor, a fluidized bed reactor, a catalytic distillation column reactor, and the like, or combinations thereof. The metathesis reactor 800 can be operated at conditions suitable for ethylene and butylenes metathesis to propylene, such as temperatures of equal to or greater than about 50° C., alternatively equal to or greater than about 100° C., alternatively equal to or greater than about 150° C., or alternatively equal to or greater than about 200° C.; pressures of from about 1 psi to about 1,500 psi, alternatively from about 10 psi to about 1,000 psi, or alternatively from about 25 psi to about 500 psi; and WHSVs of from about 0.1 $hr^{-1}$ to about 100 $hr^{-1}$, alternatively from about 1 $hr^{-1}$ to about 50 $hr^{-1}$, or alternatively from about 5 $hr^{-1}$ to about 25 $hr^{-1}$.

Nonlimiting examples of metathesis catalysts suitable for use in the present disclosure include organometallic compounds, Schrock catalysts, molybdenum alkylidenes, tungsten alkylidenes, Grubbs' catalysts, ruthenium carbenoid complexes, ruthenium carbenoid complexes modified with a chelating isopropoxystyrene ligand, Hoveyda catalysts, diphenylalkylamino based catalysts, and the like, or combinations thereof.

A process for producing cumene can comprise a step of feeding at least a portion of the benzene stream 920, and at least a portion of the first propylene stream 310 and/or at least a portion of the second propylene stream 810 to the alkylation unit 500 to produce a cumene stream 510, wherein the alkylation unit 500 comprises an alkylation catalyst, and wherein the cumene stream 510 comprises cumene.

The alkylation unit 500 can comprise any reactor (e.g., alkylation reactor) suitable for alkylating benzene with propylene to yield cumene, such as a fixed bed reactor, a fluidized bed reactor, etc.

In some aspects, the alkylation unit 500 can be operated at low temperature (e.g., less than about 135° C.) and low pressure (e.g., less than about 0.4 MPa). Benzene and propylene can be contacted in the alkylation reactor with the alkylation catalyst to produce an alkylation reactor effluent, which comprises a mixture of alkylated benzenes (e.g., cumene or isopropylbenzene) and polyalkylated benzenes (e.g., polyisopropylbenzenes). The alkylation reactor effluent can be further introduced to a transalkylation reactor comprising a transalkylation catalyst, wherein the polyisopropylbenzenes are transalkylated to cumene in the presence of benzene, and wherein a transalkylation reactor effluent is recovered from the transalkylation reactor. The alkylation reactor effluent and/or the transalkylation reactor effluent can be further introduced to a distillation system, wherein the distillation system can be designed to recover a high purity cumene product. The distillation system can recover cumene, as well as separate and recycle unconverted benzene and polyisopropylbenzenes to the alkylation reactor and/or the transalkylation reactor. The alkylation catalyst and the transalkylation catalyst can be the same or different. Nonlimiting examples of alkylation catalyst and/or transalkylation catalysts suitable for use in the present disclosure include a zeolite, β-zeolite, zeolite Y, ZSM-12, MCM-22, mordenite, and the like, or combinations thereof. The cumene production process of Polimeri Europa and Lummus Technology provides an example of cumene production from propylene and benzene, with the use of a proprietary zeolite catalyst formulation, PBE-1.

In other aspects, the alkylation unit 500 can be operated at high temperature (e.g., equal to or greater than about 150° C.) and high pressure (e.g., equal to or greater than about 1

MPa). In such aspects, the alkylation catalyst can comprise a solid phosphoric acid based catalyst.

In an aspect, a process for producing cumene as disclosed herein can be characterized by an overall cumene yield of equal to or greater than about 25 wt. %, alternatively equal to or greater than about 30 wt. %, or alternatively equal to or greater than about 40 wt. %. For purposes of the disclosure herein, all yields are calculated and reported as a weight % (wt. %) of the total weight of the plastic feed, unless otherwise specified.

In an aspect, a process for producing cumene as disclosed herein can be characterized by an overall benzene yield of equal to or greater than about 16 wt. %, alternatively equal to or greater than about 18 wt. %, alternatively equal to or greater than about 20 wt. %, or alternatively equal to or greater than about 25 wt. %. For purposes of the disclosure herein, the overall benzene yield accounts for benzene recovered at any point from the process, for example via the first $C_6$ aromatics stream 61, the second $C_6$ aromatics stream 73, from EB dealkylation, or combinations thereof. As will be appreciated by one of skill in the art, and with the help of this disclosure, the production of benzene via the benzene production system 900 can generally exceed the needs of the akylation unit, and as such benzene can also be recovered as a high value product from the process.

In an aspect, a process for producing cumene as disclosed herein can be characterized by an overall xylenes yield of equal to or greater than about 16 wt. %, alternatively equal to or greater than about 18 wt. %, alternatively equal to or greater than about 20 wt. %, or alternatively equal to or greater than about 25 wt. %.

Figure 3A:
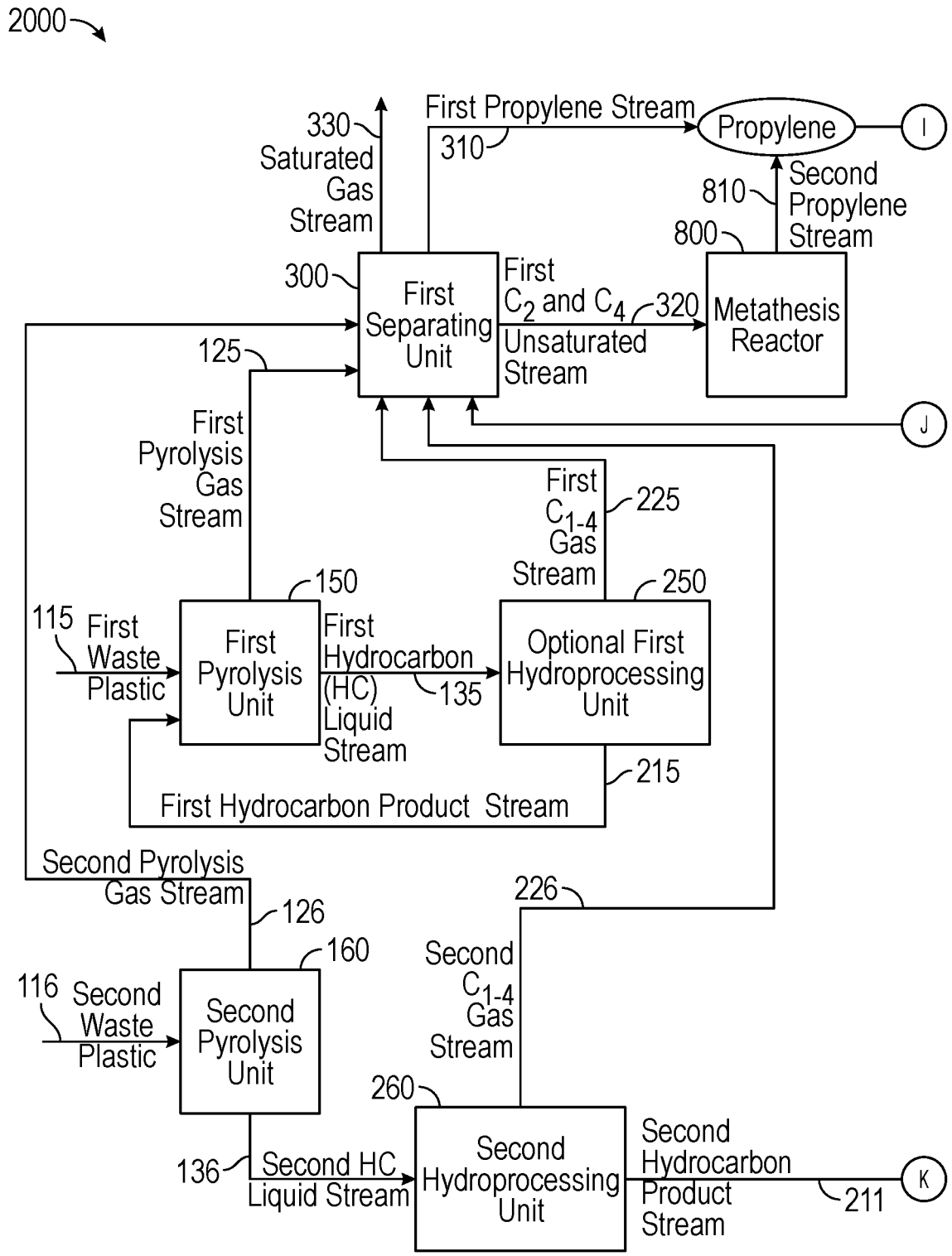
FIGS. 3A and 3B display another configuration of a system for producing cumene.
Figure 3B:
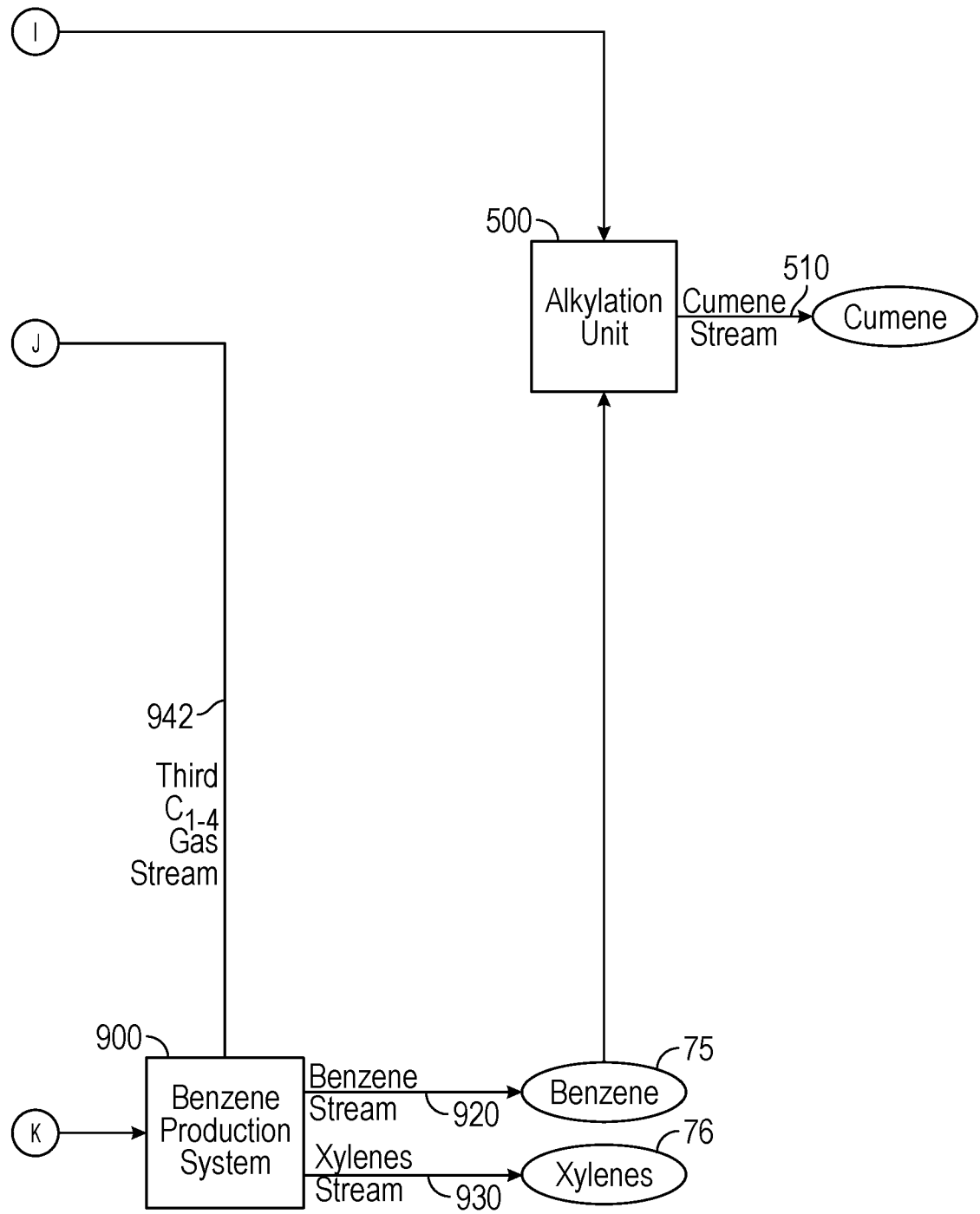

Referring to FIGS. 3A and 3B, a cumene production system 2000 is disclosed. The cumene production system 2000 generally comprises a first pyrolysis unit 150; a second pyrolysis unit 160; an optional first hydroprocessing unit 250; a second hydroprocessing unit 260; a first separating unit 300; an alkylation unit 500; a metathesis reactor 800; and a benzene production system 900.

In an aspect, a process for producing cumene can comprise (a) converting a first plastic waste stream 115 to a first hydrocarbon liquid stream 135 and a first pyrolysis gas stream 125 in the first pyrolysis unit 150, wherein the first pyrolysis unit 150 is a high severity pyrolysis unit operated at a temperature of equal to or greater than about 450° C.; (b) optionally contacting at least a portion of the first hydrocarbon liquid stream 135 with a first hydroprocessing catalyst in the presence of hydrogen in the first hydroprocessing unit 250 to yield a first hydrocarbon product stream 215 and a first $C_{1-4}$ gas stream 225, wherein the first hydrocarbon product stream 215 comprises $C_5+$ hydrocarbons; (c) recycling at least a portion of the first hydrocarbon liquid stream 135 and/or at least a portion of the first hydrocarbon product stream 215 to the first pyrolysis unit 150; (d) converting a second plastic waste stream 116 to a second hydrocarbon liquid stream 136 and a second pyrolysis gas stream 126 in the second pyrolysis unit 160, wherein the second pyrolysis unit 160 is a low severity pyrolysis unit operated at a temperature of less than about 450° C.; (e) contacting at least a portion of the second hydrocarbon liquid stream 136 with a second hydroprocessing catalyst in the presence of hydrogen in a second hydroprocessing unit 260 to yield a second hydrocarbon product stream 211 and a second $C_{1-4}$ gas stream 226, wherein the second hydrocarbon product stream 211 comprises $C_5$ to $C_8$ hydrocarbons, and wherein the first hydroprocessing catalyst and the second hydroprocessing catalyst are the same or different; (f) feeding at least a portion of the second hydrocarbon product stream 211 to the benzene production system 900 to produce a benzene stream 920 comprising benzene 75, a xylenes stream 930 comprising xylenes 76, and a third $C_{1-4}$ gas stream 942; (g) introducing at least a portion of the first pyrolysis gas stream 125, at least a portion of the second pyrolysis gas stream 126, at least a portion of the first $C_{1-4}$ gas stream 225, at least a portion of the second $C_{1-4}$ gas stream 226, at least a portion of the third $C_{1-4}$ gas stream 942, or combinations thereof to the first separating unit 300 to produce a first propylene stream 310, a first $C_2$ and $C_4$ unsaturated stream 320, and a saturated gas stream 330, wherein the first propylene stream 310 comprises propylene, wherein the first $C_2$ and $C_4$ unsaturated stream 320 comprises ethylene and butylenes, and wherein the saturated gas stream 330 comprises hydrogen and $C_1$ to $C_4$ saturated hydrocarbons; (h) feeding at least a portion of the first $C_2$ and $C_4$ unsaturated stream 320 to the metathesis reactor 800 to produce a second propylene stream 810, wherein the metathesis reactor 800 comprises a metathesis catalyst, and wherein the second propylene stream 810 comprises propylene; and (i) feeding at least a portion of the benzene stream 920, and at least a portion of the first propylene stream 310 and/or at least a portion of the second propylene stream 810 to the alkylation unit 500 to produce a cumene stream 510 comprising cumene, wherein the alkylation unit 500 comprises an alkylation catalyst. In such aspect, the process for producing cumene can be characterized by an overall cumene yield of equal to or greater than about 27 wt. %. The step (f) feeding at least a portion of the second hydrocarbon product stream 211 to the benzene production system 900 can further comprise (f1) feeding at least a portion of the second hydrocarbon product stream 211 to the reforming unit 40 to produce a reforming unit product stream 41, a third $C_{1-4}$ gas stream 942, and a hydrogen stream 43, wherein the reforming unit 40 comprises a reforming catalyst, and wherein an amount of $C_6$ to $C_8$ aromatic hydrocarbons in the reforming unit product stream 41 is greater than an amount of $C_6$ to $C_8$ aromatic hydrocarbons in the second hydrocarbon product stream 211; (f2) introducing at least a portion of the reforming unit product stream 41 to the second aromatics separating unit 50 to produce a non-aromatics recycle stream 51 and a second aromatics stream 52, wherein the second aromatics stream 52 comprises $C_6+$ aromatic hydrocarbons; (f3) recycling at least a portion of the non-aromatics recycle stream 51 to the reforming unit 40; (f4) introducing at least a portion of the second aromatics stream 52 to the third aromatics separating unit 60 to produce a benzene stream 61, a $C_7$ aromatics stream 62, a $C_8$ aromatics stream 63, a $C_9$ aromatics stream 64, a $C_{10}$ aromatics stream 65, and a $C_{11}+$ aromatics stream 66, wherein the benzene stream 61 comprises benzene, wherein the $C_7$ aromatics stream 62 comprises toluene, and wherein the $C_8$ aromatics stream 63 comprises xylenes and ethylbenzene; (f5) contacting at least a portion of the $C_7$ aromatics stream 62, at least a portion of the $C_9$ aromatics stream 64, at least a portion of the $C_{10}$ aromatics stream 65, or combinations thereof with a disproportionation and transalkylation catalyst in the presence of hydrogen in a Tatoray unit 70 to yield a third aromatics stream 71, wherein the third aromatics stream 71 comprises benzene and xylenes; and (f6) conveying at least a portion of the $C_{11}+$ aromatics stream 66 to the first hydroprocessing unit 250 and/or the second hydroprocessing unit 260. In configurations wherein the cumene production system 2000 does not comprise the optional first hydroprocessing unit 250, at least a portion of the first hydrocarbon liquid stream 135 can be (i) recycled to the first pyrolysis unit 150; (ii) conveyed to the second hydroprocessing unit 260; (iii) conveyed to the second pyrolysis unit 160; or combinations of (i)-(iii).

Processes for producing cumene as disclosed herein can advantageously display improvements in one or more process characteristics when compared to otherwise similar processes that do not employ processing plastic waste for producing both propylene and benzene, which can be further reacted to produce cumene. The processes for producing cumene as disclosed herein advantageously integrate pyrolysis, hydrocracking, reforming, olefin metathesis, and benzene alkylation to maximize production of cumene. The processes for producing cumene as disclosed herein can advantageously produce high value chemicals other than cumene, such as propylene, ethylene, butylenes, benzene, etc. Additional advantages of the process for producing cumene as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

High severity pyrolysis of mixed waste plastic was conducted to investigate the production of propylene and benzene for cumene synthesis. The mixed waste plastic had 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% was polyethylene terephthalate (PET). The pyrolysis was conducted in continuous catalytic cracking in circulating fluidized bed. The cracking was done with 57.5% spent fluid catalytic cracking (FCC) catalyst and with 42.5% ZSM-5 based zeolite additive and operated between 390-560° C. cup mix temperature of feed and catalyst. The feed rate of the plastic feed was 316 g/hr and the catalyst/feed weight ratio was about 30. In the case of a single stage pyrolysis process, the propylene content of the pyrolysis effluent was 23.7%, as it can be seen from the data in Table 1. The overall yield of light gas olefins was about 43 wt. %. The liquid product boiling below 240° C. had an aromatic concentration of 87.5 wt. %.

TABLE 1

| | Catalyst recipe<br>57.5.5% spent FCC catalyst +<br>42.5% ZSM5 zeolite catalyst<br>High severity |
|---|---|
| Avg cup mix temp [° C.] | 552.8 |
| Product yields [wt. %] | |
| H2-C4 gas | 63.4 |
| Liquids | 32.7 |
| Coke | 3.9 |
| Ethylene | 8.65 |
| Propylene | 23.7 |
| Butylene | 10.9 |

A pyrolysis oil recovered from the pyrolysis could be further fed to a hydrocracker.

Example 2

Low severity pyrolysis of mixed waste plastic was conducted to investigate the production of propylene and benzene for cumene synthesis. The mixed waste plastic had 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% was polyethylene terephthalate (PET). The mixed plastic waste was pyrolyzed as described in Example 1, except for the temperature, which was about 450° C. A pyrolysis effluent was further hydrotreated to saturate all the liquid olefins, and then was further sent to steam cracking. A hydrotreated pyrolysis liquid can typically comprise 35-45% paraffins, 35-45% iso-paraffins, 15-20% naphthenes, and 5-10% aromatics, wherein the hydrotreated pyrolysis liquid boils below 400° C. The hydrotreated pyrolysis liquid could be subjected to (i) steam cracking alone; (ii) steam cracking followed by catalytic cracking with $C_4$-$C_5$ cracking; or (iii) catalytic cracking, and in each case different yields of propylene can be obtained, as it can be seen from Table 2. Thus, it is possible to produce 50-60% light gas olefins through downstream cracking of a hydrotreated pyrolysis liquid.

TABLE 2

| Pyrolysis<br>Outputs in wt % | Steam cracker<br>product | steam cracker +<br>catalytic cracker +<br>C4, C5 cracking | catalytic<br>cracking |
|---|---|---|---|
| Methane | 14.2 | 17.3 | 13.91 |
| Hydrogen | | | |
| Ethylene | 32.8 | 34.7 | 20.71 |
| Propylene | 17.8 | 24.6 | 22.06 |
| Butylenes | | | 8.97 |
| Saturates | 16.3 | | 19.78 |
| Gasoline | 14.5 | 20.5 | 13.58 |
| Diesel | 4.4 | 2.9 | 0.99 |

Example 3

A mixed plastic waste was cracked in modular units at low severity conditions; or catalytically cracked in a circulating fluidized bed at high severity; or catalytically cracked in a circulating fluidized bed at low severity to produce a pyrolysis oil. The results from these cracking experiments are shown below. The cup mix temperature was varied between 400-600° C., specifically 450-550° C. Depending on the severity of the operation, the gases and the liquid products were separated. The composition of the cracked liquid product is shown below in the tables. The saturated hydrocarbons present in the gas were sent to gas crackers which were an ethane cracker or propane cracker. The gas cracker was selected depending on the desired end product. The cracked liquid from the pyrolysis unit was sent to hydrotreating to saturate all the liquid olefins, as this is a requirement for the liquid/naphtha cracker. Hydrotreating was performed at 300-450° C. and at a pressure of 20-100 barg using commercially available hydrotreating catalyst to produce a hydrotreated oil. The typical composition of this hydrotreated oil was 35-45% paraffins, 35-45% iso-paraffins, 15-20% naphthenes and 5-10% aromatics, with a liquid boiling below 400° C. The table below shows an example of the composition of the hydrotreated oil (e.g., hydrocarbon product stream, such as stream 210). The hydrotreated oil was then subjected to steam cracking wherein the light gas olefins were maximized and the gas saturates formed were routed to a gas cracker. In this example, 16.3 wt. % saturates produced by pyrolysis were sent to the gas cracker to form more light gas olefins, such as ethylene and propylene.

The hydrotreated oil, normally a pygas, was naphtha range material with high aromatic content. This liquid can be subjected to aromatic extraction after mild hydrogenation and a non-aromatic stream can be sent back to the naphtha/steam cracker for further cracking.

The results for a saturated pyrolysis oil feed to the steam cracker having a composition of paraffins, olefins, naphthenes, and aromatics (P/O/N/A) are shown below.

| | Catalyst recipe | | |
|---|---|---|---|
| | 80% spent FCC catalyst + 20% ZSM-5 zeolite catalyst Low severity | 80% spent FCC catalyst + 20% ZSM-5 zeolite catalyst High severity | 65% spent FCC catalyst + 35% ZSM-5 zeolite catalyst High severity |
| Avg cup mix temp, ° C. | 452 | 521 | 553.9 |
| Product yields, wt. % | | | |
| H2-C4 gas | 47.90 | 55.1 | 61.6 |
| Liquids | 43.30 | 35.9 | 31.3 |
| Coke | 8.80 | 6.2 | 5.6 |
| Light gas olefins | 28.55 | 36.61 | 41.65 |
| Gas Saturates | 17.32 | 15.93 | 17.62 |
| Gasoline | 37.00 | 30.37 | 24.54 |
| Diesel | 5.31 | 4.43 | 5.36 |
| Heavies | 0.99 | 1.06 | 1.41 |

| Product composition of mixed plastic pyrolysis after cracking | Thermally cracked from modular technology unit | Catalytically cracked from circulating fluidized bed |
|---|---|---|
| P | 45 | 9.5 |
| O | 34 | 4.2 |
| N | 11 | 3.6 |
| A | 9.4 | 82.7 |

| Product composition of mixed plastic pyrolyzed liquid after hydro treating | Thermally cracked from modular technology unit | Catalytically cracked from circulating fluidized bed |
|---|---|---|
| P | 62 | 11.6 |
| O | 0 | 0.0 |
| N | 28.6 | 5.7 |
| A | 9.4 | 82.7 |

Depending on the composition for the pyrolysis liquid, whether it is from low severity catalytic cracking from continuous circulating fluidized bed or from thermal cracking from any modular technology, an aromatic extraction unit can be positioned before the steam cracker or after the steam cracker. If the aromatic content of the pyrolysis liquid is greater 40%, having the aromatic extraction before steam cracker could minimize the coke formation and also maximize recovery of high value chemicals like benzene, toluene, xylene and ethyl benzene before sending it to steam cracker.

The products obtained from the steam cracker are displayed below at steam-to-oil (S/O) ratio of 2 wt. %, a reaction residence time of 0.1 sec, and a temperature of 850° C. For purposes of the disclosure herein, the S/O ratio refers to the ratio expressed in mass percentage of the steam added to the steam cracker per total hydrocarbon feed of the steam cracker.

| Component | Steam cracker product [wt. %] |
|---|---|
| Methane | 14.2 |
| Hydrogen | |
| Ethylene | 32.8 |
| Propylene | 17.8 |
| Butylenes | |
| Saturates | 16.3 |
| Gasoline | 14.5 |
| Diesel | 4.4 |

Example 4

This example is related to low and high severity pyrolysis of mixed waste plastic having 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% polyethylene terephthalate (PET). This experiment was conducted in a continuous catalytic cracking circulating fluidized bed. In all cases, the light gas olefins produced in the first step was greater than 28%, and saturates were also produced, which saturates can be sent directly to gas crackers to further increase the light gas olefins. The gasoline and diesel range material can be hydrotreated to saturate the liquid olefins and can be further sent to naphtha cracker. The overall make of light gas olefins combining the first stage pyrolysis followed by gas cracker for saturates and naphtha cracker for liquids can account for >60 wt. %, based on the total weight of the plastic feed (e.g., mixed waste plastic). Various catalyst recipes were tested according to the table below:

| | Catalyst recipe | | |
|---|---|---|---|
| | 80% spent FCC catalyst + 20% ZSM-5 zeolite catalyst Low severity | 80% spent FCC catalyst + 20% ZSM-5 zeolite catalyst High severity | 65% spent FCC catalyst + 35% ZSM-5 zeolite catalyst High severity |
| Avg cup mix temp. ° C. | 452 | 521 | 553.9 |
| Gas saturates feed to gas cracker | 17.32 | 15.93 | 17.62 |
| Gasoline saturates yield | 37.40 | 30.37 | 24.54 |
| C6-C8 aromatics concentration in liquid | 49.3 | 52.27 | 54.9 |
| Gasoline saturates yields after C6-C8 aromatics separation | 18.96 | 14.50 | 11.07 |

-continued

| | Catalyst recipe | | |
|---|---|---|---|
| | 80% spent FCC catalyst + 20% ZSM-5 zeolite catalyst Low severity | 80% spent FCC catalyst + 20% ZSM-5 zeolite catalyst High severity | 65% spent FCC catalyst + 35% ZSM-5 zeolite catalyst High severity |
| Diesel and heavies saturates yield | 6.30 | 5.49 | 6.77 |
| Diesel and Heavies saturates yield after hydroprocessing (calculated assuming complete saturation) | 6.69 | 5.83 | 7.19 |

The unconverted saturates can be recycled back to the cracker for further cracking and formation of light gas olefins. The pygas obtained from the naphtha cracker would be rich in aromatics which would be sent to aromatic extraction for separations of benzene, toluene, xylene (BTX) and ethylbenzene (EB) (BTX+EB).

Overall, by combining a pyrolyzer with a gas cracker and a liquid cracker, the high value chemicals like light gas olefins would be >60% and BTX+EB>15-20%.

Yields of liquid saturates in the gasoline and diesel range based on PIONA of pyrolysis oil would be sent to naphtha cracker for converting to high value chemicals. The $C_6$-$C_8$ range aromatics which are BTX+EB would be separated after hydrogenation. The higher aromatics which are normally di- and tri-aromatics would also be saturated or converted by ring opening and then a total feed consisting of gasoline saturates, diesel and heavies range saturates would be fed to the steam cracker to boost the overall yield of light gas olefins and BTX+EB range aromatics.

Example 5

Low and high severity pyrolysis of mixed waste plastic were conducted to investigate the production of aromatics. The mixed waste plastic had 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% was polyethylene terephthalate (PET). The pyrolysis was conducted in continuous catalytic/thermal cracking in circulating fluidized bed, as well as in an in-situ fluidized lab scale batch reactor. The data in first column of Table 3 provide low severity catalytic cracking results from the lab scale reactor operated at a catalyst/feed ratio of 6 and an average cup-mix temperature of about 395° C.; while the data in the remaining three columns of Table 3 show catalytic cracking data from a continuously operated circulating fluidized bed pilot unit operated as per the catalyst/feed ratios provided in Table 3. The cracking was done with different compositions of spent fluid catalytic cracking (FCC) catalyst with ZSM-5 based zeolite additive and operated between 390-560° C. cup mix temperature. In all cases, the concentration of aromatics in the liquid was greater than 75%, as it can be seen from the data in Table 3. Cracking cup mix temperature was maintained above 390° C. The data in Table 3 demonstrates that it is possible to vary the aromatics yields boiling at less than 240° C. on plastics feed basis from 20 wt. % yield to as high as 36 wt. %, with a corresponding change in yield of light gas olefins.

TABLE 3

| | Catalyst recipe | | | |
|---|---|---|---|---|
| | 62.5% spent FCC catalyst + 37.5% ZSM5 zeolite catalyst Low severity | 80% spent FCC catalyst + 20% ZSM5 zeolite catalyst Low severity | 80% spent FCC catalyst + 20% ZSM5 zeolite catalyst High severity | 65% spent FCC catalyst + 35% ZSM5 zeolite catalyst High severity |
| Avg cup mix temp, ° C. | 394.7 | 452 | 521 | 553.9 |
| Catalyst/Feed, wt./wt. | 6 | 29.4 | 48.5 | 37.2 |
| Plastic feed rate, g/hr | Batch 1.5 g feed | 295 | 282 | 273 |
| Product yields, wt. % | | | | |
| H2-C4 gas | 29.7 | 47.90 | 55.1 | 61.6 |
| Liquids | 65.0 | 43.30 | 35.9 | 31.3 |
| Coke | 5.3 | 8.80 | 6.2 | 5.6 |
| Gasoline | 45.28 | 37.00 | 30.37 | 24.54 |
| Diesel | 17.6 | 5.31 | 4.43 | 5.36 |
| Heavies | 2.1 | 0.99 | 1.06 | 1.41 |
| Total light gas olefins yield, wt. % | 16.55 | 28.55 | 36.61 | 41.65 |
| Total aromatics yield (minus 240° C. cut), wt. % | 35.6 | 30.61 | 26.07 | 20.61 |
| Aromatics conc. (minus 240° C. cut) | 78.58 | 82.74 | 85.84 | 83.97 |

Example 6

The PONA composition (e.g., paraffins, olefins, naphthenes, and aromatic compounds) in Table 4 shows the aromatic concentration from both thermally cracking in a modular low severity cracking unit at ~450° C. and catalytic cracking at an average cup mix temperature of ~452° C. with using a catalyst mixture as outlined in Example 5. The concentration of aromatics varied between 9-90%. The PONA aromatic rich stream when treated further via reforming produced high quantities of $C_6$-$C_9$ high value aromatics.

TABLE 4

| Product composition of mixed plastic pyrolysis after cracking | Thermally cracked from modular technology unit | Catalytically cracked from circulating fluidized bed |
| --- | --- | --- |
| P | 45 | 9.5 |
| O | 34 | 4.2 |
| N | 11 | 3.6 |
| A | 9.4 | 82.7 |

Example 7

Continuous cracking of mixed plastic in circulating fluidized bed reactor was conducted with different combinations of catalyst, and the results of both thermal, as well as catalytic cracking are displayed in Table 5.

TABLE 5

| Cracking type | Catalytic | Catalytic | Catalytic | Thermal | Catalytic |
| --- | --- | --- | --- | --- | --- |
| Cup mix temp (° C.) | 556.7 | 551.4 | 550.2 | 550.8 | 552.4 |
| Catalyst/Feed Ratio, wt./wt. | 40 | 41.8 | 43.4 | 33.7 | 28.8 |
| Feed rate, g/hr | 306 | 310 | 265 | 334 | 248 |
| Catalyst used | 70% Spent FCC catalyst + 30% ZSM-5 zeolite catalyst | 100% FCC spent catalyst with ~3% Rare earth content | 80% Spent FCC Catalyst + 20% ZSM-5 zeolite catalyst | Catalytically Inert material | 100% FCC spent catalyst with ~1% rare earth oxide content |
| C6 Aromatic content, wt. % | 18.04 | 14.56 | 5.31 | 2.26 | 0.36 |
| C7 Aromatic content, wt. % | 18.23 | 17.14 | 11.94 | 3.41 | 5.25 |
| C8 Aromatic content, wt. % | 25.14 | 29.45 | 31.6 | 26.27 | 35.62 |
| C6-C8 aromatic content, wt. % | 61.41 | 61.15 | 48.85 | 31.94 | 41.23 |
| C9 Aromatic content, wt. % | 10.31 | 8.74 | 17.06 | 3.51 | 21.51 |
| C10 Aromatic content, wt. % | 9.1 | 5.82 | 14.35 | 3.64 | 15.78 |
| C11 Aromatic content, wt. % | 1.54 | 3.08 | 2.26 | 0.76 | 3.38 |
| C12 Aromatic content, wt. % | 0.2 | 0.2 | 0.44 | 0.33 | 0.81 |
| C9-C12 aromatic content, wt. % | 21.15 | 17.84 | 34.11 | 8.24 | 41.48 |
| Liquid product as wt. % of plastic fed | 37.3 | 39.2 | 36 | 67.2 | 30.6 |
| Gasoline cut wt. % (221° C.) in liquid product | 82.91 | 73.36 | 71.58 | 53.96 | 63.82 |
| Diesel cut wt. % (221-370° C.) in liquid product | 15.09 | 19.36 | 26.26 | 25.70 | 31.78 |
| Heavies (370+ ° C.) | 2.00 | 7.27 | 2.16 | 20.34 | 4.40 |
| Gases yield as wt. % of plastic fed | 56.6 | 56.7 | 56.6 | 30.9 | 60.3 |
| H2 | 0.18 | 0.15 | 0.16 | 0.04 | 0.20 |
| CO2 | 1.18 | 1.62 | 1.26 | 1.47 | 0.95 |
| CO | 0.81 | 1.26 | 0.81 | 1.05 | 0.76 |
| CH4 | 0.55 | 0.42 | 0.83 | 0.95 | 1.04 |
| C2H2 | 0 | 0 | 0 | 0 | 0 |
| C2H6 | 0.9 | 0.75 | 0.99 | 1.26 | 0.97 |
| C2H4 | 8.65 | 9.46 | 7.02 | 2.39 | 5.56 |
| C3H8 | 4.8 | 4.13 | 4.08 | 0.96 | 3.39 |
| C3H6 | 19.29 | 21.71 | 18.78 | 10.89 | 22.23 |
| C4H10 (normal + iso) | 10.81 | 9.36 | 11.73 | 6.32 | 12.87 |
| C4H8 | 9.43 | 7.87 | 10.93 | 5.55 | 12.35 |
| Di-aromatics yield as wt. % of plastic fed | 6 | 5.30 | 6.84 | 10.95 | 8.32 |

TABLE 5-continued

| Cracking type | Catalytic | Catalytic | Catalytic | Thermal | Catalytic |
|---|---|---|---|---|---|
| Tri-aromatics yield as wt. % of plastic fed | 2.24 | 1.61 | 2.56 | 3.63 | 2.78 |
| Coke, wt. % | 5.7 | 1.6 | 7.0 | 1.3 | 7.6 |
| Water, wt. % | 0.4 | 2.5 | 0.4 | 0.6 | 1.5 |

The aromatic concentration in a pyrolysis product can be varied between 9 to 87 wt. %, and the concentration of $C_6$-$C_8$ aromatics can be varied between 5-62 wt. %. The $C_{9+}$ aromatics can also be varied between 8-42 wt. %. The concentration of $C_8$ aromatics alone can be greater than 35 wt. %.

Disproportionation and transalkylation of C7, C9 and C10 aromatics, mild hydrocracking or dealkylation of alkyl aromatics, or reforming of non-aromatic material can increase the formation of benzene and xylene, as can be seen from data presented in Table 5, following the schematics displayed in FIGS. 1 to 3.

The liquid boiling at less than 220° C. was 50-85 wt. %, the liquid boiling between 220-370° C. was 15-32 wt. %, and the liquid boiling above 370° C. was 2-21 wt. % of the overall liquid product for different operating cases presented in Table 5 above. These various liquid fractions could be subjected to mild hydrocracking followed by dealkylation to maximize benzene and xylene yield.

Overall, through the above examples, the processes involved in the process configuration of the integrated flowsheets as depicted in FIGS. 1-3 have been demonstrated to produce propylene and benzene that can be further used for the production of cumene.

The present disclosure is further illustrated by the following embodiments, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

The following are enumerated embodiments which are provided as non-limiting examples.

A first aspect, which is a process for producing cumene comprising: (a) converting a plastic waste to a hydrocarbon liquid stream and a pyrolysis gas stream in a pyrolysis unit; (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5$+ hydrocarbons; (c) feeding at least a portion of the hydrocarbon product to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the hydrocarbon product; (d) introducing at least a portion of the reforming unit product to a second aromatics separating unit to produce a non-aromatics recycle stream and a second aromatics stream, wherein the second aromatics stream comprises $C_6$+ aromatic hydrocarbons; (e) recycling at least a portion of the non-aromatics recycle stream to the reforming unit; (f) introducing at least a portion of the second aromatics stream to a third aromatics separating unit to produce a benzene stream, a $C_7$ aromatics stream, a $C_8$ aromatics stream, a $C_9$ aromatics stream, a $C_{10}$ aromatics stream, and a $C_{11}$+ aromatics stream, wherein the benzene stream comprises benzene, wherein the $C_7$ aromatics stream comprises toluene, and wherein the $C_8$ aromatics stream comprises xylenes and ethylbenzene; (g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes; (h) conveying at least a portion of the $C_{11}$+ aromatics stream to the hydroprocessing unit; (i) introducing at least a portion of the pyrolysis gas stream, at least a portion of the first gas stream, at least a portion of the second gas stream, or combinations thereof to a first separating unit to produce a first propylene stream, a first $C_2$ and $C_4$ unsaturated stream, and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons; (j) feeding at least a portion of the first $C_2$ and $C_4$ unsaturated stream to a metathesis reactor to produce a second propylene stream, wherein the metathesis reactor comprises a metathesis catalyst, and wherein the second propylene stream comprises propylene; and (k) feeding at least a portion of the benzene stream, and at least a portion of the first propylene stream and/or at least a portion of the second propylene stream to an alkylation unit to produce cumene, wherein the alkylation unit comprises an alkylation catalyst.

A second aspect, which is the process of the first aspect further comprising recycling at least a portion of the non-aromatics recycle stream to the pyrolysis unit.

A third aspect, which is the process of any one of the first and the second aspects further comprising introducing at least a portion of the hydrocarbon product to a first aromatics separating unit to produce a saturated hydrocarbons stream and a first aromatics stream, wherein the saturated hydrocarbons stream comprises $C_5$+ saturated hydrocarbons, and wherein the first aromatics stream comprises $C_6$+ aromatic hydrocarbons.

A fourth aspect, which is the process of the third aspect further comprising (i) conveying at least a portion of the saturated hydrocarbons stream to the reforming unit and/or (ii) conveying at least a portion of the first aromatics stream to the third aromatics separating unit.

A fifth aspect, which is the process of any one of the first through the fourth aspects, wherein an overall cumene yield is equal to or greater than about 25 wt. %.

A sixth aspect, which is the process of any one of the first through the fifth aspects further comprising recovering at least a portion of the benzene from the third aromatics stream.

A seventh aspect, which is the process of the sixth aspect, wherein an overall benzene yield is equal to or greater than about 16 wt. %.

An eighth aspect, which is the process of any one of the first through the seventh aspects further comprising recovering at least a portion of the xylenes from the $C_8$ aromatics stream.

A ninth aspect, which is the process of the eighth aspect, wherein an overall xylenes yield is equal to or greater than about 16 wt. %.

A tenth aspect, which is the process of any one of the first through the ninth aspects, wherein the step (a) of converting a plastic waste to a hydrocarbon liquid stream and a pyrolysis gas stream in a pyrolysis unit is performed at a temperature of less than about 450° C.

An eleventh aspect, which is the process of any one of the first through the tenth aspects, wherein the pyrolysis unit is a low severity pyrolysis unit.

A twelfth aspect, which is the process of any one of the first through the eleventh aspects, wherein the hydrocarbon product comprises equal to or greater than about 95 wt. % $C_8-$ hydrocarbons, based on the total weight of the hydrocarbon product.

A thirteenth aspect, which is a process for producing cumene comprising (a) converting a first plastic waste to a first hydrocarbon liquid stream and a first pyrolysis gas stream in a first pyrolysis unit; (b) optionally contacting at least a portion of the first hydrocarbon liquid stream with a first hydroprocessing catalyst in the presence of hydrogen in a first hydroprocessing unit to yield a first hydrocarbon product and a first $C_{1-4}$ gas stream, wherein the first hydrocarbon product comprises $C_5+$ hydrocarbons; (c) recycling at least a portion of the first hydrocarbon liquid stream and/or at least a portion of the first hydrocarbon product to the first pyrolysis unit; (d) converting a second plastic waste to a second hydrocarbon liquid stream and a second pyrolysis gas stream in a second pyrolysis unit; (e) contacting at least a portion of the second hydrocarbon liquid stream with a second hydroprocessing catalyst in the presence of hydrogen in a second hydroprocessing unit to yield a second hydrocarbon product and a second $C_{1-4}$ gas stream, wherein the second hydrocarbon product comprises $C_5$ to $C_8$ hydrocarbons, and wherein the first hydroprocessing catalyst and the second hydroprocessing catalyst are the same or different; (f) feeding at least a portion of the second hydrocarbon product to a reforming unit to produce a reforming unit product, a third $C_{1-4}$ gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the second hydrocarbon product; (g) introducing at least a portion of the reforming unit product to a second aromatics separating unit to produce a non-aromatics recycle stream and a second aromatics stream, wherein the second aromatics stream comprises $C_6+$ aromatic hydrocarbons; (h) recycling at least a portion of the non-aromatics recycle stream to the reforming unit; (i) introducing at least a portion of the second aromatics stream to a third aromatics separating unit to produce a benzene stream, a $C_7$ aromatics stream, a $C_8$ aromatics stream, a $C_9$ aromatics stream, a $C_{10}$ aromatics stream, and a $C_{11}+$ aromatics stream, wherein the benzene stream comprises benzene, wherein the $C_7$ aromatics stream comprises toluene, and wherein the $C_8$ aromatics stream comprises xylenes and ethylbenzene; (j) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes; (k) conveying at least a portion of the $C_{11}+$ aromatics stream to the first hydroprocessing unit and/or the second hydroprocessing unit; (l) introducing at least a portion of the first pyrolysis gas stream, at least a portion of the second pyrolysis gas stream, at least a portion of the first $C_{1-4}$ gas stream, at least a portion of the second $C_{1-4}$ gas stream, at least a portion of the third $C_{1-4}$ gas stream, or combinations thereof to a first separating unit to produce a first propylene stream, a first $C_2$ and $C_4$ unsaturated stream, and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons; (m) feeding at least a portion of the first $C_2$ and $C_4$ unsaturated stream to a metathesis reactor to produce a second propylene stream, wherein the metathesis reactor comprises a metathesis catalyst, and wherein the second propylene stream comprises propylene; and (n) feeding at least a portion of the benzene stream, and at least a portion of the first propylene stream and/or at least a portion of the second propylene stream to an alkylation unit to produce cumene, wherein the alkylation unit comprises an alkylation catalyst.

A fourteenth aspect, which is the process of the thirteenth aspect, wherein the step (a) of converting a first plastic waste to a first hydrocarbon liquid stream and a first pyrolysis gas stream in a first pyrolysis unit is performed at a temperature of equal to or greater than about 450° C.

A fifteenth aspect, which is the process of any one of the thirteenth and the fourteenth aspects, wherein the step (d) of converting a second plastic waste to a second hydrocarbon liquid stream and a second pyrolysis gas stream in a second pyrolysis unit is performed at a temperature of less than about 450° C.

A sixteenth aspect, which is the process of any one of the thirteenth through the fifteenth aspects, wherein an overall cumene yield is equal to or greater than about 27 wt. %.

A seventeenth aspect, which is the process of any one of the thirteenth through the sixteenth aspects further comprising recovering at least a portion of the benzene from the third aromatics stream.

An eighteenth aspect, which is the process of the seventeenth aspect, wherein an overall benzene yield is equal to or greater than about 18 wt. %.

A nineteenth aspect, which is the process of any one of the thirteenth through the eighteenth aspects further comprising recovering at least a portion of the xylenes from the $C_8$ aromatics stream.

A twentieth aspect, which is the process of the nineteenth aspect, wherein an overall xylenes yield is equal to or greater than about 18 wt. %.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing cumene comprising:
   (a) converting a plastic waste to a hydrocarbon liquid stream and a pyrolysis gas stream in a pyrolysis unit;
   (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons;
   (c) feeding at least a portion of the hydrocarbon product to a reforming unit to produce a reforming unit product, a second gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the hydrocarbon product;
   (d) introducing at least a portion of the reforming unit product to a second aromatics separating unit to produce a non-aromatics recycle stream and a second aromatics stream, wherein the second aromatics stream comprises $C_6+$ aromatic hydrocarbons;
   (e) recycling at least a portion of the non-aromatics recycle stream to the reforming unit;
   (f) introducing at least a portion of the second aromatics stream to a third aromatics separating unit to produce a benzene stream, a $C_7$ aromatics stream, a $C_8$ aromatics stream, a $C_9$ aromatics stream, a $C_{10}$ aromatics stream, and a $C_{11}+$ aromatics stream, wherein the benzene stream comprises benzene, wherein the $C_7$ aromatics stream comprises toluene, and wherein the $C_8$ aromatics stream comprises xylenes and ethylbenzene;
   (g) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes;
   (h) conveying at least a portion of the $C_{11}+$ aromatics stream to the hydroprocessing unit;
   (i) introducing at least a portion of the pyrolysis gas stream, at least a portion of the first gas stream, at least a portion of the second gas stream, or combinations thereof to a first separating unit to produce a first propylene stream, a first $C_2$ and $C_4$ unsaturated stream, and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons;
   (j) feeding at least a portion of the first $C_2$ and $C_4$ unsaturated stream to a metathesis reactor to produce a second propylene stream, wherein the metathesis reactor comprises a metathesis catalyst, and wherein the second propylene stream comprises propylene; and
   (k) feeding at least a portion of the benzene stream, and at least a portion of the first propylene stream and/or at least a portion of the second propylene stream to an alkylation unit to produce cumene, wherein the alkylation unit comprises an alkylation catalyst.

2. The process of claim 1, further comprising recycling at least a portion of the non-aromatics recycle stream to the pyrolysis unit.

3. The process of claim 1, further comprising the step of introducing at least a portion of the hydrocarbon product to a first aromatics separating unit to produce a saturated hydrocarbons stream and a first aromatics stream, wherein the saturated hydrocarbons stream comprises $C_5+$ saturated hydrocarbons, and wherein the first aromatics stream comprises $C_6+$ aromatic hydrocarbons.

4. The process of claim 3, further comprising (i) conveying at least a portion of the saturated hydrocarbons stream to the reforming unit and/or (ii) conveying at least a portion of the first aromatics stream to the third aromatics separating unit.

5. The process of claim 1, wherein an overall cumene yield is equal to or greater than about 25 wt. %.

6. The process of claim 1, further comprising the step of recovering at least a portion of the benzene from the third aromatics stream.

7. The process of claim 6, wherein an overall benzene yield is equal to or greater than about 16 wt. %.

8. The process of claim 1, further comprising the step of recovering at least a portion of the xylenes from the $C_8$ aromatics stream.

9. The process of claim 8, wherein an overall xylenes yield is equal to or greater than about 16 wt. %.

10. The process of claim 1, wherein the step (a) of converting a plastic waste to a hydrocarbon liquid stream and a pyrolysis gas stream in a pyrolysis unit is performed at a temperature of less than about 450° C.

11. The process of claim 1, wherein the pyrolysis unit is a low severity pyrolysis unit.

12. The process of claim 1, wherein the hydrocarbon product comprises equal to or greater than about 95 wt. % $C_{8-}$ hydrocarbons, based on the total weight of the hydrocarbon product.

13. A process for producing cumene comprising:
   (a) converting a first plastic waste to a first hydrocarbon liquid stream and a first pyrolysis gas stream in a first pyrolysis unit;
   (b) optionally contacting at least a portion of the first hydrocarbon liquid stream with a first hydroprocessing catalyst in the presence of hydrogen in a first hydroprocessing unit to yield a first hydrocarbon product and a first $C_{1-4}$ gas stream, wherein the first hydrocarbon product comprises $C_5+$ hydrocarbons;
   (c) recycling at least a portion of the first hydrocarbon liquid stream and/or at least a portion of the first hydrocarbon product to the first pyrolysis unit;
   (d) converting a second plastic waste to a second hydrocarbon liquid stream and a second pyrolysis gas stream in a second pyrolysis unit;
   (e) contacting at least a portion of the second hydrocarbon liquid stream with a second hydroprocessing catalyst in the presence of hydrogen in a second hydroprocessing unit to yield a second hydrocarbon product and a second $C_{1-4}$ gas stream, wherein the second hydrocarbon product comprises $C_5$ to $C_8$ hydrocarbons, and wherein the first hydroprocessing catalyst and the second hydroprocessing catalyst are the same or different;
   (f) feeding at least a portion of the second hydrocarbon product to a reforming unit to produce a reforming unit product, a third $C_{1-4}$ gas stream, and a hydrogen stream, wherein the reforming unit comprises a reforming catalyst, and wherein an amount of $C_6$ to $C_8$ aromatic hydrocarbons in the reforming unit product is greater than an amount of $C_6$ to $C_8$ aromatic hydrocarbons in the second hydrocarbon product;

(g) introducing at least a portion of the reforming unit product to a second aromatics separating unit to produce a non-aromatics recycle stream and a second aromatics stream, wherein the second aromatics stream comprises $C_6$+ aromatic hydrocarbons;

(h) recycling at least a portion of the non-aromatics recycle stream to the reforming unit;

(i) introducing at least a portion of the second aromatics stream to a third aromatics separating unit to produce a benzene stream, a $C_7$ aromatics stream, a $C_8$ aromatics stream, a $C_9$ aromatics stream, a $C_{10}$ aromatics stream, and a $C_{11}$+ aromatics stream, wherein the benzene stream comprises benzene, wherein the $C_7$ aromatics stream comprises toluene, and wherein the $C_8$ aromatics stream comprises xylenes and ethylbenzene;

(j) contacting at least a portion of the $C_7$ aromatics stream, at least a portion of the $C_9$ aromatics stream, at least a portion of the $C_{10}$ aromatics stream, or combinations thereof with a disproportionation and transalkylation catalyst in the presence of hydrogen in a disproportionation and transalkylation unit to yield a third aromatics stream, wherein the third aromatics stream comprises benzene and xylenes;

(k) conveying at least a portion of the $C_{11}$+ aromatics stream to the first hydroprocessing unit and/or the second hydroprocessing unit;

(l) introducing at least a portion of the first pyrolysis gas stream, at least a portion of the second pyrolysis gas stream, at least a portion of the first $C_{1-4}$ gas stream, at least a portion of the second $C_{1-4}$ gas stream, at least a portion of the third $C_{1-4}$ gas stream, or combinations thereof to a first separating unit to produce a first propylene stream, a first $C_2$ and $C_4$ unsaturated stream, and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons;

(m) feeding at least a portion of the first $C_2$ and $C_4$ unsaturated stream to a metathesis reactor to produce a second propylene stream, wherein the metathesis reactor comprises a metathesis catalyst, and wherein the second propylene stream comprises propylene; and (n) feeding at least a portion of the benzene stream, and at least a portion of the first propylene stream and/or at least a portion of the second propylene stream to an alkylation unit to produce cumene, wherein the alkylation unit comprises an alkylation catalyst.

14. The process of claim 13, wherein the step (a) of converting a first plastic waste to a first hydrocarbon liquid stream and a first pyrolysis gas stream in a first pyrolysis unit is performed at a temperature of equal to or greater than about 450° C.

15. The process of claim 13, wherein the step (d) of converting a second plastic waste to a second hydrocarbon liquid stream and a second pyrolysis gas stream in a second pyrolysis unit is performed at a temperature of less than about 450° C.

16. The process of claim 13, wherein an overall cumene yield is equal to or greater than about 27 wt. %.

17. The process of claim 13, further comprising the step of recovering at least a portion of the benzene from the third aromatics stream.

18. The process of claim 17, wherein an overall benzene yield is equal to or greater than about 18 wt. %.

19. The process of claim 13, further comprising the step of recovering at least a portion of the xylenes from the $C_8$ aromatics stream.

20. The process of claim 19, wherein an overall xylenes yield is equal to or greater than about 18 wt. %.

* * * * *